(12) United States Patent
Coleman et al.

(10) Patent No.: US 10,898,099 B2
(45) Date of Patent: Jan. 26, 2021

(54) CHARACTERIZING GASTROINTESTINAL FUNCTIONS FROM SURFACE ELECTROPHYSIOLOGY RECORDING

(71) Applicant: The Regents of the University of California, Oakland, CA (US)

(72) Inventors: Todd Prentice Coleman, La Jolla, CA (US); Armen Gharibans, San Diego, CA (US)

(73) Assignee: THE REGENTS OF THE UNIVERSITY OF CALIFORNIA OAKLAND, CA, Oakland, CA (US)

( * ) Notice: Subject to any disclaimer, the term of this patent is extended or adjusted under 35 U.S.C. 154(b) by 291 days.

(21) Appl. No.: 15/770,393

(22) PCT Filed: Oct. 24, 2016

(86) PCT No.: PCT/US2016/058534
§ 371 (c)(1),
(2) Date: Apr. 23, 2018

(87) PCT Pub. No.: WO2017/070700
PCT Pub. Date: Apr. 27, 2017

(65) Prior Publication Data
US 2018/0317800 A1 Nov. 8, 2018

Related U.S. Application Data

(60) Provisional application No. 62/245,441, filed on Oct. 23, 2015.

(51) Int. Cl.
*A61B 5/0488* (2006.01)
*A61B 5/0492* (2006.01)
*A61B 5/00* (2006.01)

(52) U.S. Cl.
CPC ........ *A61B 5/04884* (2013.01); *A61B 5/0492* (2013.01); *A61B 5/42* (2013.01);
(Continued)

(58) Field of Classification Search
CPC ........... A61B 5/04884; A61B 5/04012–04014; A61B 5/0402; A61B 5/0408;
(Continued)

(56) References Cited

U.S. PATENT DOCUMENTS 5,795,304 A 8/1998 Sun et al.
9,943,264 B2 4/2018 Axelrod et al.
(Continued)

OTHER PUBLICATIONS

Ba, D. et al., "Robust spectrotemporal decomposition by iteratively reweighted least squares", PNAS, vol. 111, No. 50, 2014, pp. E5336-E5345.
(Continued)

*Primary Examiner* — Thaddeus B Cox
(74) *Attorney, Agent, or Firm* — Perkins Coie LLP

(57) ABSTRACT

Methods, systems, and devices are disclosed for characterizing the gastrointestinal functions using non-invasive surface recordings from EGG. In one aspect, a system for non-invasively characterizing gastrointestinal functions is disclosed. The system includes electrodes configured to capture a gut electrophysiology recording; and a processor to estimate a frequency and an amplitude of the recording across time.

16 Claims, 21 Drawing Sheets

(52) U.S. Cl.
CPC .......... *A61B 5/6823* (2013.01); *A61B 5/6833* (2013.01); *A61B 5/721* (2013.01); *A61B 5/725* (2013.01); *A61B 5/7225* (2013.01); *A61B 5/0075* (2013.01); *A61B 5/7253* (2013.01); *A61B 5/7257* (2013.01); *A61B 5/7275* (2013.01); *A61B 5/742* (2013.01); *A61B 2562/0219* (2013.01); *A61B 2562/04* (2013.01)

(58) Field of Classification Search
CPC ... A61B 5/0478; A61B 5/0492; A61B 5/0432; A61B 5/0488; A61B 5/4233; A61B 5/4238; A61B 5/4255; A61B 5/4806–4818; A61B 5/72–726; A61M 21/00–02
See application file for complete search history.

(56) References Cited

U.S. PATENT DOCUMENTS

| | | | |
|---|---|---|---|
| 2006/0173364 | A1 | 8/2006 | Clancy et al. |
| 2008/0139953 | A1 | 6/2008 | Baker et al. |
| 2010/0298741 | A1 | 11/2010 | Gross et al. |
| 2011/0106203 | A1 | 5/2011 | Markowitz et al. |
| 2011/0295096 | A1 | 12/2011 | Bibian et al. |
| 2012/0136224 | A1* | 5/2012 | Najarian ............. A61B 5/726 600/301 |
| 2013/0046150 | A1 | 2/2013 | Devanaboyina |
| 2015/0289822 | A1 | 10/2015 | Dugan |
| 2015/0313502 | A1* | 11/2015 | Mestha ............. A61B 5/02007 600/473 |
| 2016/0007871 | A1* | 1/2016 | Sanger ............. A61B 5/0004 600/546 |
| 2016/0338634 | A1* | 11/2016 | Neu ............. A61B 5/04884 |

OTHER PUBLICATIONS

Koch, K.L. et al., "Gastric Dysrhythmias and Nausea of Pregnancy", Dig. Dis. Sci., vol. 35, No. 8, 1990, pp. 961-968.

Parkman, H.P. et al., "Electrogastrography: a document prepared by the gastric section of the American Motility Society Clinical GI Motility Testing Task Force," Neurogastroenterol Motil, 2003, vol. 15, No. 2, pp. 89-102.

Ravelli, A.M. et al., "Vomiting and gastroesophageal motor activity in children with disorders of the central nervous system", J. Pediatr. Gastroenterol. Nutr., vol. 26, No. 1, 1998. pp. 56-63.

Riezzo, G. et al., "Electrogastrography in Adults and Children: the Strength, Pitfalls, and Clinical Significance of the Cutaneous Recording of the Gastric Electrical Activity," Biomed Res Int, vol. 2013, p. 282757, 2013.

Szarka, L.A. et al., "Methods for measurement of gastric motility," Am. J. Physiol. Gastrointest. Liver Physiol., vol. 296, No. 3, pp. G461-G475, Mar. 2009.

Verghagen, M.A. et al., "Pitfalls in the Analysis of Electrogastrographic Recordings," Gastroenterology, vol. 117, No. 2, pp. 453-460, Aug. 1999.

International Search Report and Written Opinion for PCT Application No. PCT/US2016/058534, dated Feb. 27, 2017, 12 pages.

Extended European Search Report for European Patent Application No. 16858460.5, dated Apr. 4, 2019, 8 pages.

Abid, S. et al. "Electrogastrography: Poor correlation with antroduodenal manometry and doubtful clinical usefulness in adults" World Journal of Gastroenterology, Oct. 14, 2007; 13(38): pp. 5101-5107.

Rodriguez, L. "Chapter 15: Electrogastrography, Breath Tests, Ultrasonography, Transit Tests, and SmartPill" Pediatric Neurogastroenterology, 2013, pp. 163-176.

* cited by examiner

CHARACTERIZING GASTROINTESTINAL FUNCTIONS FROM SURFACE ELECTROPHYSIOLOGY RECORDING

CROSS-REFERENCE TO RELATED APPLICATIONS

This patent document is a 35 U.S.C. § 371 National Stage application of International Application No. PCT/US2016/058534 entitled "CHARACTERIZING GASTROINTESTINAL FUNCTIONS FROM SURFACE ELECTROPHYSIOLOGY RECORDING" filed Oct. 24, 2016, which claims benefit of priority of U.S. Provisional Patent Application No. 62/245,441 entitled "CHARACTERIZING GASTROINTESTINAL FUNCTIONS FROM SURFACE ELECTROPHYSIOLOGY RECORDING" filed on Oct. 23, 2015. The entire contents of the aforementioned patent applications are incorporated by reference as part of the disclosure of this patent document.

TECHNICAL FIELD

This patent document relates to electrophysiology surface recordings.

BACKGROUND

Various existing clinical tools to diagnose most gastrointestinal (GI) diseases are invasive or require radiation. The endoscopy is a common GI diagnostic procedure, where a catheter is inserted through the mouth, down the esophagus and into the stomach. This technique can be used to detect visual abnormalities (e.g., inflammation, obstruction) or take a biopsy for analysis, but cannot assess GI functions. Tests that assess GI functions include the gastric emptying test or manometry procedure. Gastric emptying tests typically measure how quickly the stomach empties a radioactively labeled meal and the percentage of the meal remaining in the stomach is imaged and recorded for an extended period (e.g., 4 hours in some instances). Abnormalities assessed by this test include dumping syndrome (i.e. stomach emptying too quickly) or gastroparesis (i.e. delayed stomach emptying with no obstruction). However, some implementations for this test suffer from drawbacks such as poor repeatability, inconclusivity if the patient vomits during the test, and the required use of radioactive materials.

Another example of a GI test is an invasive manometry procedure to assess GI functions, in which a catheter is placed either through the mouth/nose or anus, and pressure sensors placed along the catheter are used to measure the physical contractions in the GI system. Due to the difficulty of administering the test and interpreting the test results, this test tends to be available through a small number of skilled gastroenterologists.

The recording of the electrophysiology (i.e. recording body surface potentials using a biopotential amplifier) is a method of characterizing various bodily functions. For example, a 12-lead electrocardiogram (ECG) can be used to characterize cardiac functions and the electroencephalogram (EEG) can be used to characterize brain function. Similar attempts were made to non-invasively record electrophysiology in the GI system using electrogastrogram (EGG). However, EGG has not been widely used in clinical settings due to its poor correlation with gastric emptying tests, antroduodenal manometry, and the actual disease status, along with inconsistent results, poor signal quality, etc. Moreover, a high exclusion rate of patients have resulted from unpredictable results due to motion artifacts or other unknown factors. These issues related to EGG are reported in many publications, such as Verhagen et al., *Gastroenterology* 117(2): 453-460 (1999), Abid et al., *World J. Gastroenterol.* 13(38): 5101-5107 (2007), and Rodriguez, *Pediatric Neurogastroenterology* (4): 163-176 (2013). Most insurance companies consider EGG experimental and investigational because their clinical utility has not been established.

The lack of reliability of EGG is due to several challenges that have been difficult to overcome:

1) Amplitude of the recorded signal is relatively weak (e.g., 50-200 µV);

2) The EGG signal is contaminated by signals from the heart, respiration, movement, and other gastrointestinal organs; and 3) There is a significant amount of inter-subject variability in stomach anatomy; consequently, standard electrode placement has not yet been established.

SUMMARY

There is a need in the art for reliable, non-invasive systems, methods, and protocols to measure gastrointestinal physiology in real time to accurately assess GI functions. The technology disclosed herein can be implemented in various configurations to address this need and to be used in various applications.

Disclosed are methods, systems, and devices that characterize gastrointestinal (GI) functions using non-invasive surface recordings from electrogastrography (EGG).

In one aspect, a system for non-invasively characterizing gastrointestinal functions is disclosed. The system includes electrodes to capture a gut electrophysiology recording and a processor to estimate a frequency and an amplitude of the recording across time.

The system can be implemented in various ways to include one or more of the following features. For example, the processor can use additional data to build a more accurate estimate of the frequency and amplitude. The additional data can include imaging data, context, or previous medical history. The processor can provide information to the user using a statistical method. The processor can use a robust spectrotemporal estimation method to estimate the frequency and the amplitude of the EGG recording. The processor can use a robust spectrotemporal estimation method that includes formulating a Bayesian estimation problem with a prior distribution that yields maximum a posteriori (MAP) spectral estimates. The electrodes can record the gut electrophysiology using Electrogastrography (EGG). The electrodes can include a single bipolar pair. The electrodes can include an array of electrodes. A placement of the single bipolar pair or an array of electrodes can be optimized based on gut anatomy.

BRIEF DESCRIPTION OF THE DRAWINGS

FIG. 1 shows examples of GI monitoring systems and features based on the disclosed technology.

FIG. 5 illustrates examples of data collection and analysis in connection with the GI monitoring systems shown in FIGS. 1A-1C and FIGS. 2-4.

FIG. 16 demonstrates that a patient having pyloric spasm/intermittent obstruction was correctly identified based on the different GI pattern over a 24-hour period of time from that of healthy subjects.

DETAILED DESCRIPTION

Exemplary Features in Physiological Monitoring

Figure 1A:
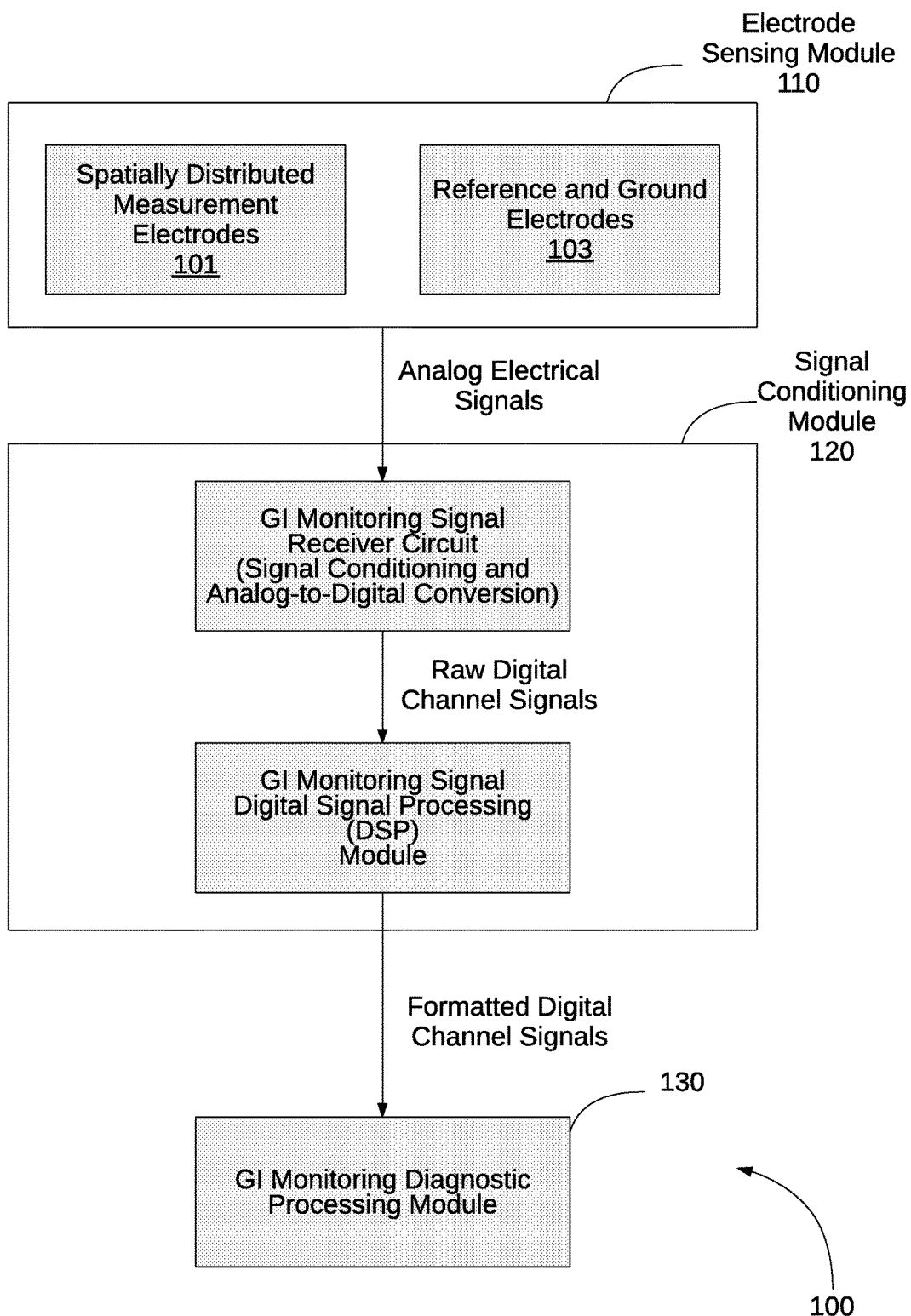
FIG. 1A shows an example of a GI monitoring system including three basic modules: an electrode sensing module 110 that has different measurement electrodes 101 and reference and ground electrodes 102 placed at different locations on a subject to obtain electrical signals representing GI activities of the subject under monitoring; a GI signal conditioning module 120 that amplifies, processes and digitizes the signals from the electrodes 101 to produce digital GI channel signals for processing and diagnostic extraction; and a GI monitoring diagnostic processing module 130 that processes the digital GI channel signals from the module 120 to perform digital signal processing techniques to extract statistical features in the GI activities.

Disclosed herein is a system for non-invasive characterization of GI functions of a patient or a subject. In this disclosure, the term "subject" or "patient" is used interchangeably to mean a person or a mammal whose GI functions are monitored and analyzed using the technology disclosed herein. The system includes one or more sensors configured to acquire electrophysiological data from a subject and a data processing unit configured to receive and process the electrophysiological data. The electrophysiological data acquired by the system as disclosed in this document includes the electrogastrogram (EGG), which records the electrical signals generated by the stomach, and the intestinal electrogram (sometimes called the electroenterogram (EEnG)), which records the electrical signals generated by the intestines.

As used herein, a "single-channel" monitoring system comprises one electrochemical sensor that includes one measurement electrode for obtaining measurements. An electrochemical sensor in typical implementations operates by using its measurement electrode in a combination with a reference electrode and a ground electrode (sometimes referred to as a patient reference signal, a patient reference, a return, or a patient return) to produce a single-channel signal. Each measurement electrode produces a single channel or signal that can be represented by a waveform (e.g. time-series waveform, or a frequency domain waveform) obtained from the output of the measurement electrode of such a sensor relative to the reference electrode. A "multichannel" or "multiple channel" monitoring system can produce multiple waveforms (e.g. time-series waveforms, or frequency domain waveforms) from different measurement electrodes within a single sensor. Some configurations can include two or more sensors, where each sensor can produce one or more single-channel signals. Different sensors may share a common reference electrode and/or a common ground electrode.

A GI system that implements the disclosed technology can be used to provide a real time monitoring capability of the GI electrophysiology for a desired period of time in an ambulatory setting. For example, the monitoring period can be less than 1 hour, up to 1 hour, up to 2 hours, up to 3 hours, up to 4 hours, up to 5 hours, up to 6 hours, up to 8 hours, up to 12 hours, up to 16 hours, up to 20 hours, up to 24 hours, up to 48 hours, up to 72 hours. Such a system may be implemented in various configurations to meet specific diagnostic needs or application requirements. For example, such a system may be configured as a wearable device that can be worn by or attached to a subject for continuous health or lifestyle monitoring in real time for a desired period, e.g., many days. This wearable system allows GI activity monitoring outside the hospital or clinical settings which may cause undesired stress on patients leading to extra GI activities that may not be directly associated with the patients' medical conditions. As such, this wearable system can be advantageously used to obtain more objective measurements during a patient's routine activities at home or other locales where the patient carries on routine daily activities.

In implementations, a physiological monitoring system disclosed herein includes one or more sensors, each of which transmits a signal over a wired or wireless conduit or communication link or medium to a data processing unit that includes a processor and memory. In some implementations, a single-channel measurement can produce a single waveform of voltage data on the surface of the skin. For example, the measurement and reference electrodes are placed on the skin overlaying the GI organ(s) of interest. In this disclosure, the GI organs of interest include, for example, stomach, small intestines, and large intestines.

In some embodiments, the measurement electrode is placed on a subject's midline between the xiphoid and umbilicus, the reference electrode is placed to the right of the measurement electrode (e.g., about 4 to 5 cm in some instances), and the ground electrode is placed on the left costal margin or hip. The difference between the readings of the measurement electrode and the reference electrode is taken and amplified by an amplifier in a signal conditioning module such that the "noise" common to both electrodes is cancelled out. The resulting time-series of voltage data is collected and analyzed according to the methods disclosed herein. EGG parameters are then extracted from the subsequent spectrotemporal analysis.

Figure 1B:
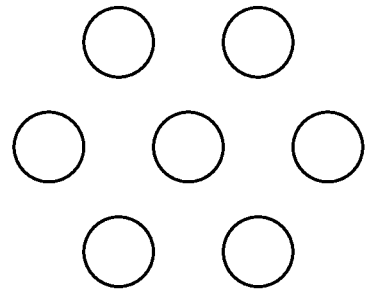
FIG. 1B shows two examples of multiple measurement electrode configurations. Configuration A is an example of a sensor with 16 measurement electrodes arranged in a square grid. Configuration B is an example of a sensor with 7 measurement electrodes in a near circular arrangement.
Figure 1B:
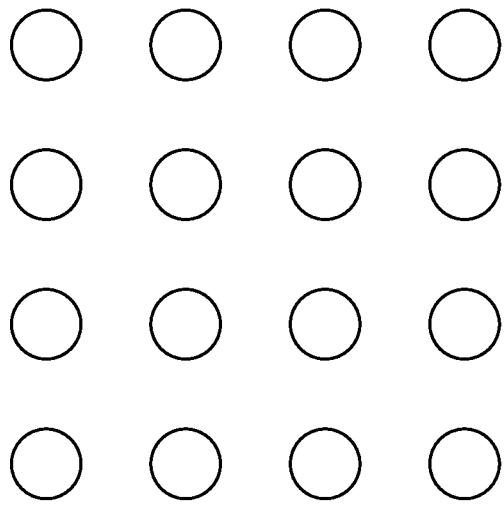
Figure 1C:
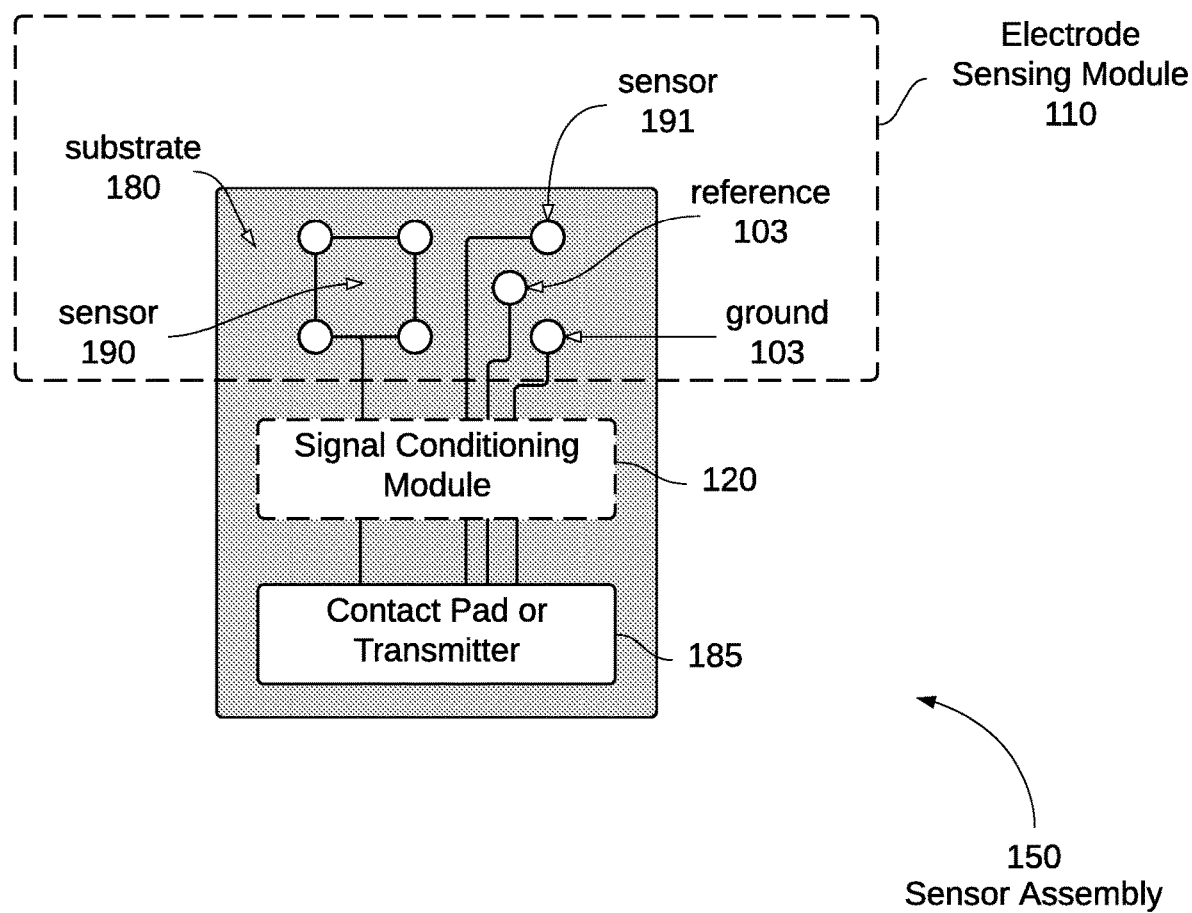
FIG. 1C is an example of a sensor assembly that implements the GI monitoring system in FIG. 1A. The assembly shown includes multiple sensors 190, 191, and the reference and ground electrodes 130. The sensor 190 is shown as a sensor having four measurement electrodes while sensor 191 has one measurement electrode.

FIGS. 1A, 1B and 1C show examples of GI monitoring systems and features based on the disclosed technology. FIG. 1A shows an example of a GI monitoring system including three basic modules: (1) an electrode sensing module 110 that has different measurement electrodes 101 and reference and ground electrodes 103 placed at different locations on a subject to obtain electrical signals representing GI activities of the subject under monitoring; (2) a signal conditioning module 120 that amplifies, filters, processes, digitizes, and down-samples the signals from the electrode sensing module 110 to produce digital GI channel signals for processing and diagnostic extraction; and (3) a GI monitoring diagnostic processing module 130 that processes the digital GI channel signals from the module 120 to perform digital signal processing techniques to extract statistical features in the GI activities. The details of those modules 110, 120 and 130 are explained in examples in later section of this document.

In implementation, the GI signal conditioning module 120 can be one or more devices placed in a doctor's office or clinical facility or as a portable device carried by a patient or a wearable device directed attached to the patient's body. The module 120 may include, depending on the needs or requirements of applications, analog signal conditioning circuitry such as a power supply, amplifiers, filters and analog-to-digital conversion unit, multiplexers, data storage, and a data processing unit. In some implementations, one or more displays and a user interface panel may be included. The module 120 may also include communication ports that can be connected via one or more communication conduits or links. In some applications, the GI monitoring diagnostic processing module 130 can be a local device with one or more microprocessors and desired storage to carry out the data analyses to produce desired output. In other applications, the GI monitoring diagnostic processing module 130 can be one or more remote servers connected in one or more computer or communication networks to carry out the data analyses to produce desired output.

In some embodiments, a system implementation may use two or more measurement electrodes to produce two or more channels of data. For example, the total number of measurement electrodes can be selected based on the specific GI monitoring needs or requirements and, in some cases, up to 30 measurement electrodes or 512 measurement electrodes may be used based on the disclosed technology. Some applications can be designed to use measurement electrodes ranging from 2 to 6, 8, 16, 25, 32, 64, 128, 256, or 512.

There are advantages to using multiple measurement electrodes. For example, additional measurement electrodes can provide more spatial sensing coverage at different locations in connection with the monitored organ. Since there is a significant amount of anatomical variability between subjects, by adding more sensors to cover a larger surface area, the measurement electrodes at different locations can more accurately record the electrophysiology the GI organ(s) of interest. When the electrodes are placed farther from the organ, the signal amplitude decreases due to the attenuation of the signal as it conducts through a longer distance in the body. Therefore, using more measurement electrodes at selected different locations provides more measurements at such different locations to improve the GI monitoring accuracy. For another example, additional measurement electrodes can be used to reduce undesired noise and artifacts (which may be caused by motion of the subject or other factors) in the signal with appropriate analytical techniques.

There is, however, a trade-off with respect to the number of measurement electrodes in some applications. For example, an excess number of measurement electrodes is not desirable because too many electrodes can be obtrusive, cause a subject to feel uncomfortable, and trigger unwanted subject stress that may impact the GI activities. For a given target monitoring area, increasing the number of measurement electrodes beyond a certain number may also limit the practical physical size of each electrode so that the size of each electrode should be reduced to provide sufficient spacing between different electrodes. Smaller electrodes have higher impedances relative to larger electrodes and this increased impedance due to reduction in electrode size can lead to an increase in the signal noise.

In addition to designing the system with proper number and locations of measurement electrodes, various configurations of the measurement electrodes are possible with multiple channel monitoring based on other parameters or considerations of the GI system designs. For example, measurement electrodes can be spatially arranged as an array to cover or substantially cover the organ of interest. In some embodiments, the measurement electrodes are placed in proximity of the organ of interest such that the organ is substantially covered by the measurement electrodes, for example, at least 25% covered, at least 50% covered, at least 75% covered, at least 80% covered, at least 90% covered, at least 95% covered, or about 100% covered. In some embodiments, the measurement electrodes are placed over an organ part that has the strongest electrophysiological signals. As an example, if the functions of a subject's stomach are evaluated, the measurement electrodes can be placed at or near the antrum.

The shape of the array can be configured to provide desired GI monitoring. For another example, the array of the measurement electrodes can be in suitable shapes to cover the organ of interest, for example, in the shape of a circle, a square, a rectangle, or a certain irregular shape. In some embodiments, the configuration of the measurement electrodes is based on the anatomy of a particular organ of interest such that the coverage by the electrodes can be determined on an individual basis and may vary from patient to patient. In some embodiments, the configuration of the measurement electrodes can be determined by information of a subject's organ based on actual imaging of the organ obtained via a suitable imaging technique, such as CT imaging, MRI, ultrasound, optical imaging and others. In a multiple channel GI monitoring configuration, different sensors can share a common reference electrode and a common ground electrode, which can be placed at a suitable location on the subject's body surface. In some embodiments when a multiple channel configuration is used, one of the measurement electrodes can be designated as the reference electrode. The ground electrode reduces interference and improves patient safety.

FIG. 1B shows two examples of multiple measurement electrode configurations. Configuration A is an example of a sensor with 16 measurement electrodes arranged in a square grid. Configuration B is an example of a sensor with 7 measurement electrodes in a near circular arrangement.

FIG. 1C is an example of a sensor assembly that implements the GI monitoring system in FIG. 1A. The assembly shown includes multiple sensors 190 and 191. The sensor 190 is shown as a sensor having four measurement electrodes, while sensor 191 is shown as a sensor having one measurement electrode. The reference and ground electrodes 103 are also shown. In some implementations, the signal conditioning module 120 can be part of the sensor assembly, as shown in FIG. 1C, and it can include an analog-to-digital converter (ADC) to transform the signal from analog format to digital format (i.e., analog signal to digital signal), one or more amplifiers to amplify the signal, and one or more signal filters to further condition the signal, such as reducing the signal noise. In various implementations, a substrate 180 may be used to provide a support for the sensor electrodes and may be, in some applications, an adhesive substrate that can be used to mount the assembly directly onto the skin.

In some embodiments, the electrodes are arranged in a fixed configuration in which the spatial relationship of the electrodes remain unchanged before and after being placed on the patient. For example, the electrodes can be fixed on a support before being placed on a subject's body surface. In other embodiments, the electrodes are arranged in an adjustable configuration, meaning that the spatial relationship of the electrodes can be adjusted when placed on the subject.

The system disclosed herein includes a data processing unit that process the signals produced by the sensors and electrodes. In some embodiments of the system, the sensor assembly includes a signal conditioning module having an amplifier to amplify the signals acquired by the measurement electrodes of the sensors. The sensor assembly amplifies each signal before providing the amplified signal to the data processing unit. Whereas in some embodiments, the data processing unit can include a signal conditioning module having an amplifier to amplify the received signal from the sensor assembly. In some embodiments, the signal conditioning module of the data processing unit further amplifies the received amplified signal from the sensor assembly. Multi-stage amplification can further enhance the weak signal against the background noise during transmission and processing. In some embodiments, the system further includes a display such that the data processing unit can communicate the processed signals to the display. In certain implementations, the data processing unit can communicate the processed signals to a mobile device or save the data locally for offline processing.

The data processing unit may be designed to carry out any number of processing steps for operation of the system. In addition, the data processing unit may be configured to receive and process data received via the input. For example, the data processing unit may be configured to assemble a time-frequency representation of signals from the electrophysiological data, such as EGG data, acquired from a subject. The data processing unit can incorporate a digital filter that filters the signal to a specific frequency band of interest. The data processing unit can also down-sample the data for more efficient storage and transmission. Additionally, the data processing unit can perform any desirable noise rejection to filter any interfering signals associated with the data, using one or more sensors. The data processing unit can also be configured to receive an indication, via the input, related to a particular patient profile, such as a patient's age, height, weight, gender, etc. In some aspects, the output may include a display configured to provide information or indicators with respect to de-noised spectral decompositions, that may be formulated using spectrotemporal representations, either intermittently or in real time. The data processing unit can also extract features from the data, including one or more of dominant frequency and power, fasting-fed power ratio, percentage of normal slow waves, percentage of dysrhythmias, instability coefficient of dominant frequency and power, or percentage of power distribution.

The components of the systems disclosed herein, including the sensors or electrodes, data processing unit, displays, data storage, mobile device, etc., can be connected via one or more communication conduits or other suitable linking devices. In some implementations, the conduits and linking devices can be replaced by wireless connections between components. The sensors or electrodes may be integrated with the signal conditioning module, as shown in FIG. 1C.

In some embodiments, a system implementation can further include a device such as a mobile device or smartphone. The mobile device, via communication to the data processing unit, can be used to start and/or terminate the recording of the data. In some embodiments, a physical switch or button on the system can be used to start and stop data logging. The system can also be configured to start logging data automatically when power is connected and stop logging automatically when power is disconnected, or to start and stop at pre-specified times. The data can be transmitted to the mobile device via wired or wireless transmission, which can process the data locally or upload the data to a computer or server for processing. The mobile device can display information to the user and examples of the information that can be displayed include electrode contact impedance values, time-series data, signal quality, spectral estimation, estimated features, etc. An application on the mobile device can be used to time-stamp events, such as meals, bowel movements, sleep, exercise, activity, symptoms, etc. In some embodiments, events can also be marked using buttons on the system or by user's input. These event markers can then be combined with the data in the analysis. For example, if someone is experiencing nausea and logs that symptom on the mobile device, the data slightly before and after that event can be analyzed and correlated with any abnormalities. Another example is when an abnormality in the gut is detected with the noninvasive recording, the events slightly before and after that time can be analyzed to determine the causality of the abnormality. For example, sometimes a meal can cause abnormalities. The mobile device can also provide real-time feedback to a user, for example, how the subject reacts to a certain type of food, treatment, etc.

In some embodiments, the system further includes an accelerometer and/or a gyroscope. An accelerometer and gyroscope can provide movement and orientation information, respectively. Knowledge of a subject's movement and/or posture can provide useful information for the analysis. For example, it can be determined whether the subject is sleeping or awake. Also, the probability of artifact in the signal is higher when the subject is moving. The information provided by the accelerometer and/or gyroscope can be used to provide information to the de-noising and artifact removal algorithm. For example, when motion is high, there is a higher chance of artifact in the signal. The data processing unit can be used to receive and process data from different sources, or to indicate that the signal to noise ratio in this window of time is low, such that a Bayesian estimation procedure can take advantage of this to extract relevant spectrotemporal features.

Figures 2, 2A, 2B:
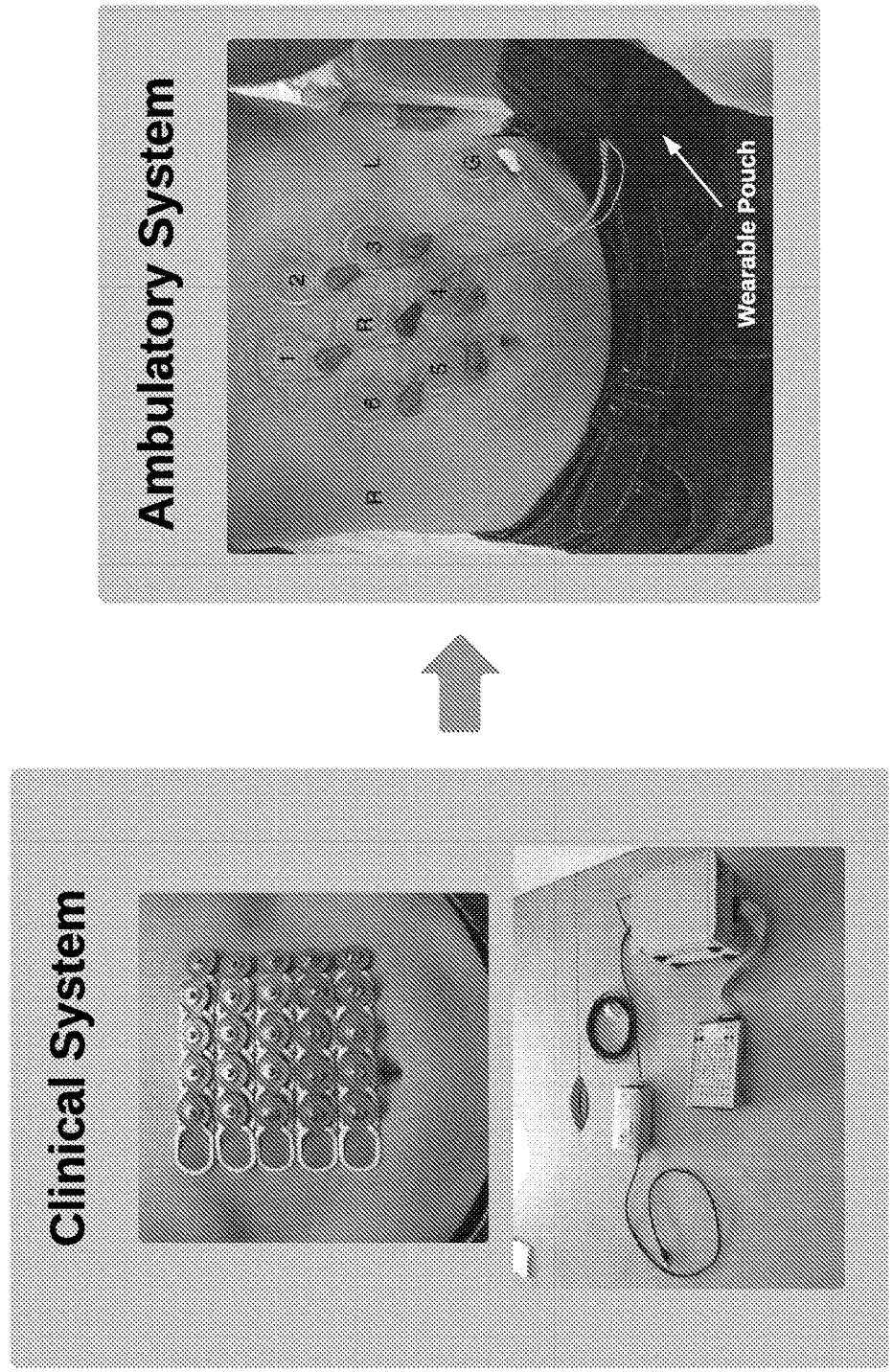
FIG. 2 illustrates a portable device including one or more sensors connected to a compact data processing unit, power source (e.g. battery, inductive power, solar power), and local data storage (e.g. memory card, flash storage) that fit into a small pouch that can be worn on the body around the waist.
FIG. 2A shows a clinical system including a GI sensor array with sensors arranged in a square array on a flexible substrate that is attachable to a patient's skin and an image of the GI signal conditioning module.
FIG. 2B shows an ambulatory system including a wearable GI sensor array with sensors arranged in a circular array on a flexible substrate that is attachable to a patient's skin and a wearable pouch for holding the GI signal conditioning module.

The system disclosed herein can be configured into a portable device providing ambulatory monitoring of GI physiology at a non-clinical setting in addition to a clinical setting. For example, such a portable device includes one or more sensors connected to a compact data processing unit, power source (e.g. battery, inductive power, solar power), and local data storage (e.g. memory card, flash storage) that fit into a small pouch that can be worn on the body around the waist, as shown in FIG. 2. FIG. 2A shows a clinical system including a GI sensor array with sensors arranged in a square array on a flexible substrate that is attachable to a patient's skin and an image of the GI signal conditioning module. FIG. 2B shows an ambulatory system including a wearable GI sensor array with sensors arranged in a circular array on a flexible substrate that is attachable to a patient's skin and a wearable pouch for holding the GI signal conditioning module.

In various implementations, the portable device includes wireless transmission capabilities (e.g. WiFi, Bluetooth, etc.) to another device for storage and processing. In some embodiments, the entire system, including sensor(s), data processing unit, and power source, can be miniaturized to fit onto an adhesive substrate that is worn on the body. The system including the portable device can be paired with a mobile device, and can also include instructions for use and recommendations to the user. For example, if a certain pattern is detected, the user should consume a diet, medication, etc. or avoid consumption of the diet or medication.

Figure 3:
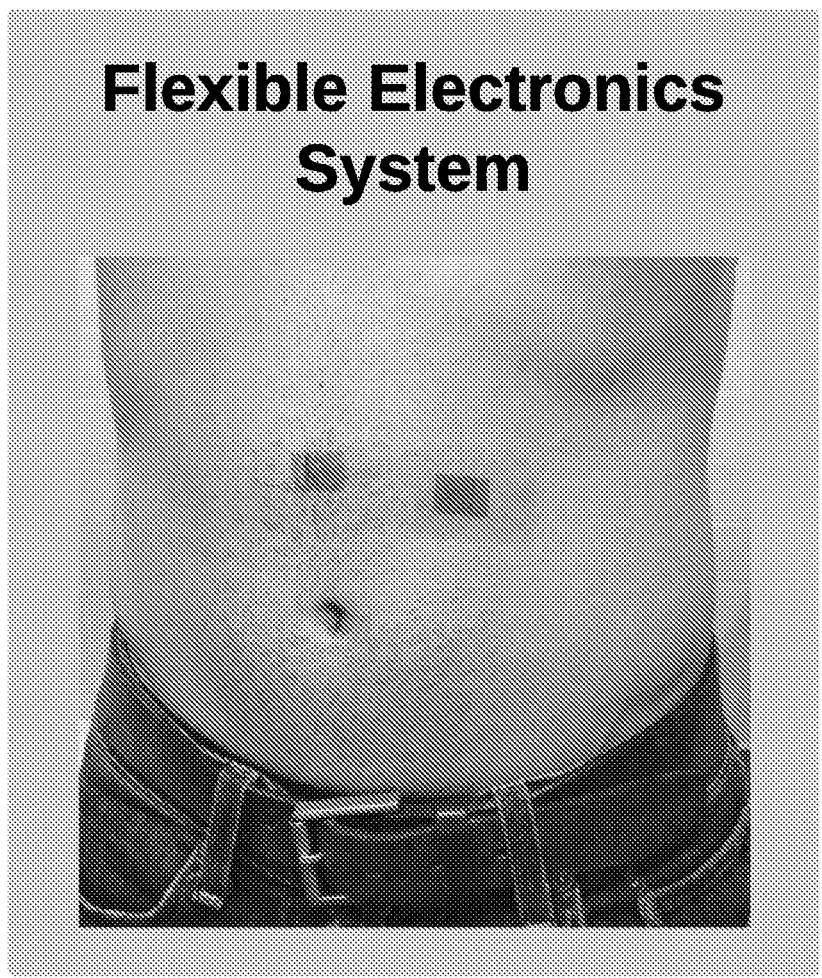
FIG. 3 shows an example of a flexible single-channel system including measurement and reference electrodes configured to record the EGG signal.

In some embodiments, the sensor can be made of thin, flexible and/or stretchable electronics embedded in a flexible and/or stretchable substrate. The sensor can contain multiple electrodes in a suitable configuration. Various components, such as amplifiers, processors, local storage, and wireless chips can also be embedded in these systems, to produce a complete minimally obtrusive wearable system. In some embodiments, the flexible substrate can be mounted on the skin of the subject. The measurement and reference electrodes from a flexible single-channel system configured to record the EGG signal are shown in FIG. 3.

Figure 4:
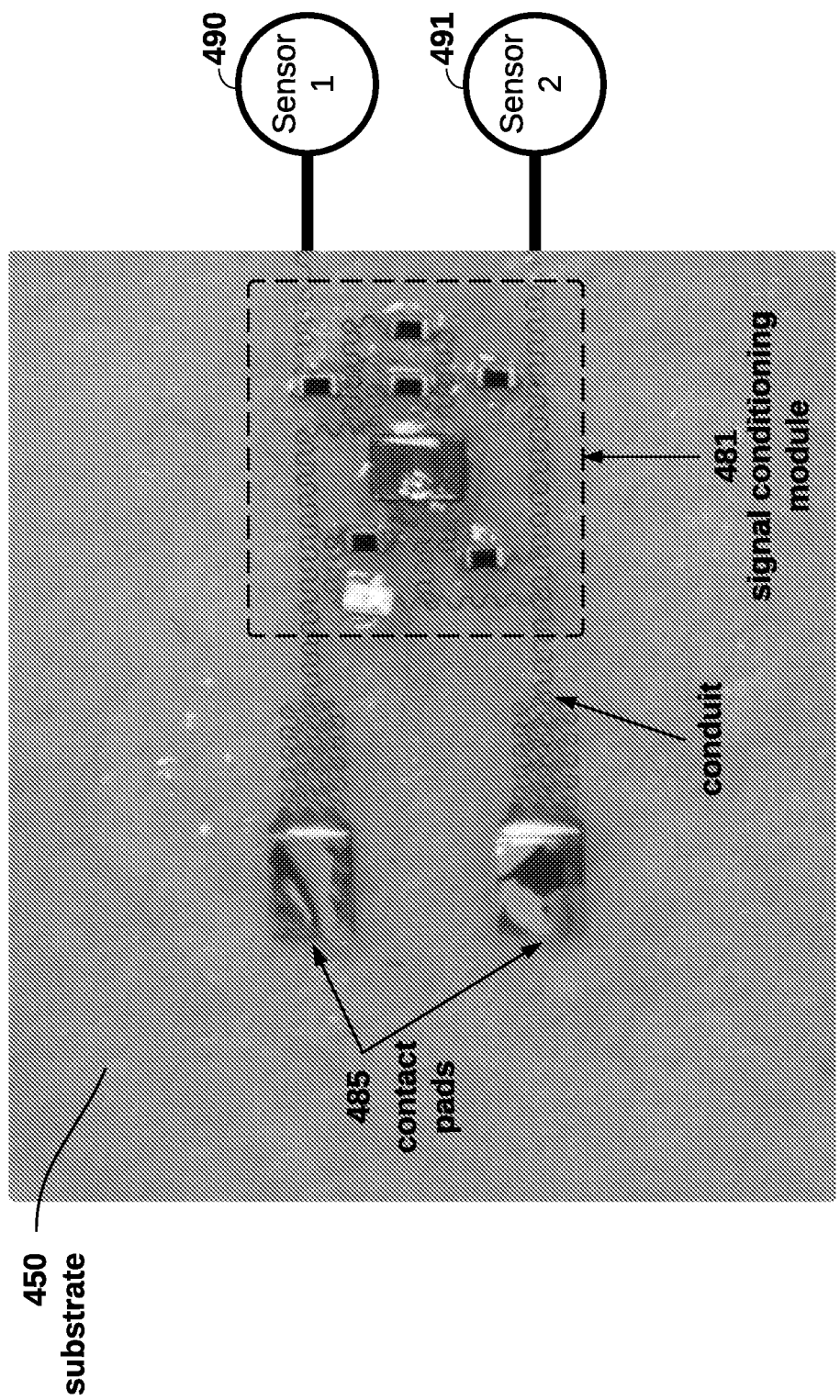
FIG. 4 shows an example of a flexible sensor assembly with two sensors 490 and 491. A signal conditioning module 481 is integrated directly into a flexible substrate 450, which is mounted on the skin. The contact pads 485 are used to transmit the data to a data processing unit.

FIG. 4 shows an example of a flexible sensor assembly with two sensors, 490 and 491. A signal conditioning module 481 is integrated directly into a flexible substrate 450, which is mounted on the skin. The contact pads 485 are used to transmit the data to a data processing unit.

The flexible sensor assembly with embedded circuit components shown in FIG. 4 enables the use of high-density electrode arrays for GI monitoring. Flexible sensors can be designed using microfabrication techniques at the nanometer scale, enabling any arbitrary configuration and size of electrodes. This enables the reduction in size of each individual electrode, thus allowing for more electrodes per unit area. In some embodiments, a multiplexing unit, or mux, can also be included into the flexible sensor assembly or the data processing unit. Typical systems sample and digitize the analog biopotentials at certain frequencies, e.g., above 250 Hz, well over the Nyquist frequency required for GI electrophysiology. Since the range of GI frequencies are relatively low (e.g. less than 1 Hz), multiplexing of a high number of electrodes can be accomplished with existing processing and amplifier architectures. Moreover, the multiplexing allows for adaptive electrically connecting electrodes, to make the effective electrode size and shape configurable via software operation (i.e. groups of electrodes can be combined to effectively increase the electrode area and signal quality). As such, this capability enables adaptive, high-resolution electrode configurations, where the electrical connection between sensors can be changed. For example, electrodes can be dynamically selected to localize the GI signals on the abdominal surface, which is useful since GI organs can move (e.g. stomach volume can change greatly after a large meal). Since most GI signals are very low frequency, this also enables the transmission of many electrical waveforms across bandwidth-constrained links.

Data Collection and Analysis

FIG. 5 illustrates examples of data collection and analysis in connection with the GI monitoring systems shown in FIGS. 1A-1C and FIGS. 2-4.

Figure 5A:
FIG. 5A shows an exemplary process for characterizing GI function from surface recordings.

FIG. 5A shows an exemplary process for characterizing GI function from surface recordings. A single bipolar pair or an array of electrodes is used to record the gut electrophysiology. The placement of these electrodes is optimized based on gut anatomy. A robust spectrotemporal estimation method is used to estimate the frequency and amplitude (power) of the EGG recording across time. Additional information such as imaging data, context, and previous medical history may also be used to build a more accurate estimate. Statistical methods are used to convey meaningful and actionable information to the user.

Figure 5B:
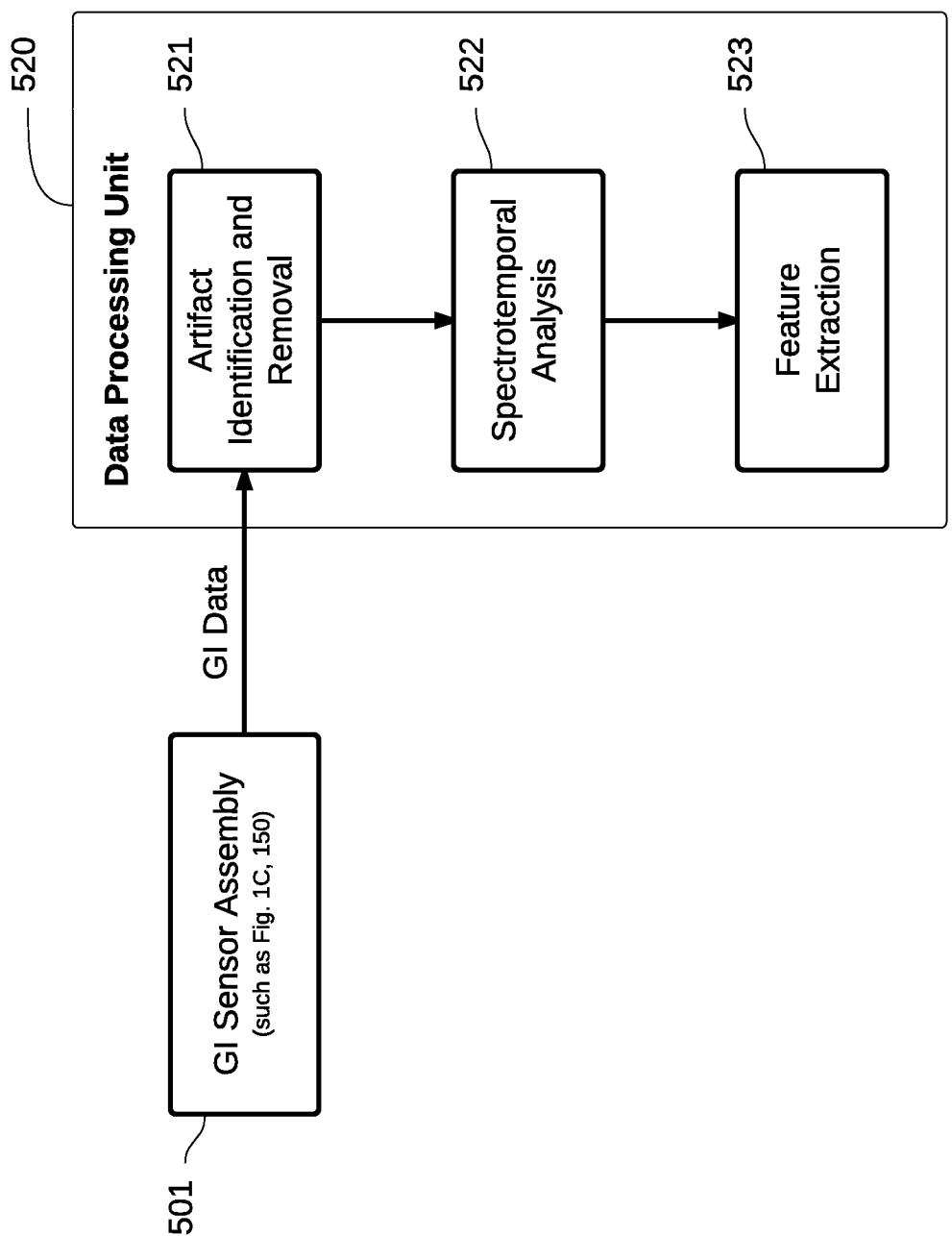
FIG. 5B is a flow chart of an exemplary method to process the GI data collected from the sensor assembly and extract actionable features from the data.

FIG. 5B is a flow chart of an exemplary method to process the GI data collected from the sensor assembly and extract actionable features from the data. The steps include collection of GI data by the sensor assembly 501 that is output to the data processing unit 520. The data processing unit automatic identifies and removes detrimental artifacts contained in the signal in module 521. Next the data processing unit converts the time-domain data to a spectrotemporal, or spectrogram, representation in module 522 to enable the identification of GI signals based on their characteristic frequencies. Finally, relevant features from the spectrogram can be extracted in module 523. Examples of features include dominant frequency and power across time, fasting-fed power ratio, percentage of normal slow waves activity throughout recording, percentage of dysrhythmias, instability coefficient of dominant frequency and power, and percentage of power distribution.

I) Single-Channel EGG

A) Input

As disclosed above, the electrophysiological data related to GI functions generated by the sensor assembly can be collected and sent to the data processing unit. In this example, the input is a single time-series of GI voltage data. This is represented by the output of 501 in FIG. 5.

B) Artifact Identification and Removal

The EGG signal is relatively weak (e.g., 50-200 µV in some cases). Therefore, the signal must be significantly amplified, which makes it susceptible to noise and undesired signals superimposed on the biopotential recordings, often referred to as artifacts in the signal. Non-motion-related artifacts usually originate from external interference, such as 60 Hz power lines, electrosurgical units, other equipment and broadcast stations. Motion-related artifacts may originate in adjacent nerve and muscle, in the skin, in the electrode, and in the cable. Electrodes typically consist of a conductive paste or gel to improve signal condition of surface potentials. Skin motion is a major source of motion artifact, since skin potential changes with pressure on the skin. Likewise, cable movement can cause motion artifact by deformations of the cable insulation, which acts as a piezoelectric movement transducer. Signals generated by the contraction of abdominal muscles, which are between the sensors and GI organs are a major source of artifact. This signal can be orders of magnitude larger than the biopotentials generated by the GI organs.

The artifacts in the signal have severely hindered the utility of EGG in clinical practice. Even in subjects that were asked to remain still, there is typically a high-exclusion rate of data due to motion artifact, as described previously by Verhagen et al., *Gastroenterology* 117(2): 453-460 (1999) in a study with 148 subjects.

Analog or digital filters (e.g. band-pass, low-pass, and notch filters) can be used to remove artifact from sources at higher frequencies. For example, since the typical frequencies of the GI potentials are very low (i.e. less than 1 Hz), the 60 Hz powerline noise can be removed with a notch or low-pass filter without effecting the signal. Motion artifacts, though, can span across all frequencies. Therefore, they cannot be completely removed by filtering alone.

In the single-channel recordings, machine learning algorithms can be utilized as one approach for identifying and removing artifacts in the signal by recognizing patterns in the signal. Machine learning techniques such as support vector machine, artificial neural network, fuzzy inference system, and clustering can be used for automatic identification of artifacts. In general, to train a machine learning algorithm, one can divide a set of time-series data into small windows (e.g. five seconds of data) and appropriately label each window with the presence of artifact. The trained machine learning algorithm can then be applied to new time-series data to automatically label windows with artifact. In addition, this type of analysis can provide a probability of the presence of artifact associated with each window.

C) Spectral Estimation

Disclosed herein is a method for analyzing data produced by the system. The technology disclosed herein entails robust spectral analysis of the data.

Spectral analysis is an important tool for analyzing EGG data. Unlike ECG and EEG, time-domain EGG waveforms are difficult to analyze, since the signals are at very low frequencies with no unique morphology, such as the QRS complex in ECG. As described herein, this document provides an algorithm to compute a de-noised time-varying spectral decomposition of a signal. Conventional spectral estimation techniques use sliding windows to enforce smoothness and continuity of the estimated spectra. The spectral estimates using these techniques exhibit a significant amount of noise. In one configuration, a state-space model is used that naturally promotes smoothness of the estimated spectrotemporal representation of the data and performs de-noising. Quantitatively, the state-space formulation leads to a principled statistical framework that uses the data to determine the optimal amount of smoothing. Qualitatively, the algorithm results in spectral estimates that are significantly sharper and less noisy than those obtained using classical spectral estimation techniques.

The disclosed technology provides for a drastic improvement on how to characterize GI functions from surface recordings. The disclosed technology can be used to accurately characterize the dynamics of GI function that correlate with disease, with dietary intakes, effects of various drugs, etc. This information can be extracted from a robust spectrotemporal representation of surface electrode recordings, a method to identify the frequency of peristalsis as well as its amplitude. The disclosed technology exploits the fact that there are primarily few dominant frequency bands pertaining to peristalsis within the physiological signals produced by the sensors and electrodes, thus producing more robust time-frequency estimates.

Consider the $y_t$, a real-valued signal, for example, a single-channel time-series of EGG, where $t=1, 2, \ldots, T$. The signal may be obtained by sampling the underlying, continuous-time, noise-corrupted signal at a rate $f_s$ (above the Nyquist rate). Given an arbitrary interval of length W, let:

$$y_n \equiv (y_{(n-1)W+1}, y_{(n-1)W+2}, \ldots, y_n W) \text{ for } n=1,2,\ldots,N$$

where N is defined as $T/W$.
Consider the following spectrotemporal representation of the signal y:

$$y_n = \tilde{F}_n \tilde{x}_n + v_n$$

where, $v_n$ is independent, identically-distributed, additive zero-mean Gaussian noise and:

$$(F_n)_{l,k} \triangleq \cos\left(2\pi((n-1)W+l)\frac{k-1}{K}\right)$$

$$(F_n)_{l,k+K/2} \triangleq \sin\left(2\pi((n-1)W+l)\frac{k-1}{K}\right)$$

where $v_n$ is independent, identically-distributed, additive zero-mean Gaussian noise. With this representation, x can be viewed as a time-frequency representation of the non-stationary signal y. The objective is to compute an estimate of x given the data y. This is computed by solving the following maximum a posteriori (MAP) estimation problem:

$$\max_{x_1,\ldots,x_N} -\sum_{n=1}^{N} \frac{1}{2\sigma^2} \|y_n - F_n x_n\|_2^2 + f(x_1, x_2, \ldots, x_N)$$

where, $f(x_1, x_2, \ldots, x_N) \triangleq \log p_i(x_1-x_0, x_2-x_1, \ldots, x_N-x_{N-1})$ is the log-likelihood given by our measurement model, and $p_i$ is a general penalty function that utilizes prior knowledge on the temporal dynamics of the latent variable.

For example, in our case the prior knowledge on the temporal dynamics of the latent variable could reflect the fact that electrophysiology of the stomach is in a narrow frequency band near 0.05 Hz, suggesting that many of the spectrotemporal coefficients outside the band are near zero. As some patients may have a peristalsis band near 0.045 Hz and others at 0.053 Hz, the prior $p_i$ can encode the fact that a small number of coefficients are zero, but which ones are not known a priori.

In one embodiment, we may anticipate that the spectrotemporal activity is piecewise smooth across time, then the penalty function can be represented as:

$$\log p_1(w_1, w_2, \ldots, w_N) = -\alpha \sum_{k=1}^{K} \left(\sum_{n=1}^{N} w_{n,k}^2 - \epsilon^2\right)^{\frac{1}{2}} + c_1$$

where $\alpha>0$ and $\epsilon$ is a positive constant. This can be solved with efficient convex optimization methods. The inner sum can be viewed as a $l_2$-norm on the change in frequency coefficients over time in a given frequency band (enforcing continuity) and the outer sum can be viewed as a $l_1$-norm across frequencies. As a result, many rows of w will be exceedingly close to zero. Thus, many of the rows of w are linearly dependent and w is necessarily low rank.

Next, consider an alternative penalty function that does not make any explicit assumptions regarding the spectral or temporal structure of the signal, but instead isolates the aspect of $p_i$ that ensures w is low rank. It is well known that direct rank-minimization is an NP-hard problem. Consider, instead, penalizing by the nuclear norm of w:

$$\log p_2(w_1, w_2, \ldots, w_N) = -\beta \|w\|_*$$

where $\beta>0$. It has been shown that minimizing the nuclear norm yields the smallest convex envelope of the rank-minimization problem and can recover the exact minimum rank solution under certain assumptions. This more general scenario with the nuclear norm allows for sparsity in frequency and continuity in time. It also allows for situations that are piece-wise continuous in time, thus enabling temporal change points (e.g. due to rapid GI dysfunctions).

Several algorithms can be used to solve the robust spectral estimation framework described above. One example method includes the "spectrotemporal pursuit algorithm," which yields estimates of time-varying frequency coefficients that are smooth in time and sparse in frequency, using the $p_1$ prior described above. Another example method includes the "low-rank spectrotemporal decomposition (LRSD) algorithm," which yields estimates whose transitions are low-rank, using the $p_2$ prior described above. The LRSD estimate can yield the row-sparse estimates of spectrotemporal pursuit when the data fits such a model, but is flexible in that it can represent a broader class of data, such as signals that have abrupt changes in spectral activity, which can happen with GI electrophysiology. Moreover, these two problems can be solved with an efficient alternating direction method of multipliers (ADMM) framework, which is a method that solves convex optimization problems by breaking them into smaller pieces, each of which are easier to compute. In this instance, the imposition of the respective penalty functions is delegated to an isolated step in the algorithm. As a result, the final update of spectrotemporal pursuit requires shrinking rows of the current estimate of the transition variables, while the final update of LRSD involves soft-thresholding the singular values of these variables.

Thus, disclosed herewith is an improvement comparing to the standard STFT approach for determining the dominant frequency of a physiological data recording. By formulating a Bayesian estimation problem with various prior distributions, the system and method disclosed herein can achieve more robust estimates of EGG frequency and amplitude. Example 1 below shows the application of this approach to real data, demonstrating its utility.

Non-parametric methods, such as multitaper spectral estimation, can also be used for creating a de-noised spectrotemporal estimate of the data. The multitaper overcomes some of the limitations of conventional Fourier analysis. By obtaining multiple independent estimates from the same sample, this method reduces estimation bias. Each data taper is multiplied element-wise by the signal to provide a windowed trial from which one estimates the power at each component frequency. The multitaper spectral estimate formed by averaging the corresponding N tapered estimates would have a variance reduced by a factor of N.

D) Feature Extraction

The summary parameters provided by typical EGG analyses do not characterize all the dynamics of GI functions and it does not enable the clinician to make an accurate diagnosis. Statistical methods can be used as described in this document including, but not limited to, change point detection and Bayesian estimation of the posterior distribution for uncertainty quantification. These statistical techniques are used with prolonged recording times that are enabled by the technology disclosed herewith.

II) Multi-Channel EGG

A) Input

As disclosed above, the electrophysiological data related to GI functions generated by the sensor assembly can be collected and sent to the data processing unit. In this instantiation, the input is multiple time-series of GI voltage data collected from multiple sensors. This is represented by the output of 501 in FIG. 5.

B) Artifact Identification and Removal

In some embodiments, the data analysis method disclosed herewith can be applied to multiple channels (i.e. multiple waveforms) of GI data. The data analysis method can combine the information from multiple channels for an improvement in artifact removal prior to the spectrotemporal estimation.

One way for using multiple channels for artifact removal is treating it as a blind source separation (BSS) problem. BSS is the separation of a set of source signals from a set of mixed signals, without the aid or with very little aid of information about the source signals or the mixing process. Using established mathematics in signal processing, the mixing of the signals can be estimated, and the two separate sets of signals can be extracted.

Given the nature of the signal and underlying physiology, independent component analysis (ICA) is a candidate for removing artifacts from the EGG. ICA is a subtype of BSS with underlying assumptions that the subcomponents are non-Gaussian signals and that they are statistically independent from each other. EGG recordings appear to satisfy most of the conditions for ICA: 1) current from different sources is mixed linearly at the EGG electrodes; 2) time delays in signal transmission are negligible, due to the well-established quasi-static assumption for bioelectric phenomena in the human body; 3) there appear to be fewer sources than mixtures, even when accounting for different GI organs; and 4) sources have non-Gaussian voltage distributions. Artifacts, such as those introduced by small movements of the electrical contacts should be reasonably independent of signals originating from the GI organs. Signals generated by different parts of the GI organs can also be separated by ICA if they are generated at different times or if there is jitter in the relative timing of overlapping signal sources. Example 2 is an application of BSS to multi-channel EGG data, showing the ability of BSS to remove artifacts in the signal.

III) Additional Inputs

Figure 6:
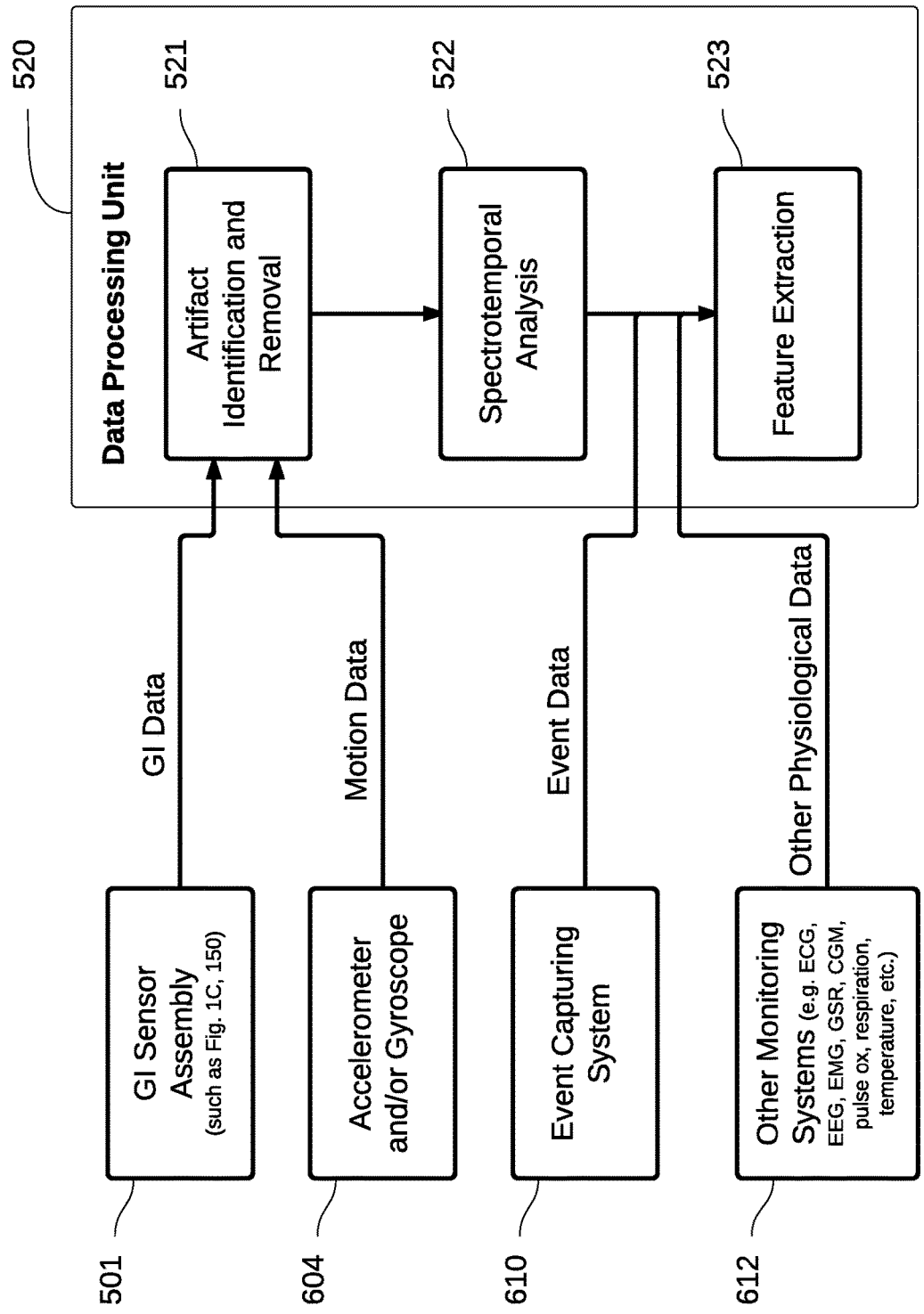
FIG. 6 is a flow chart of an exemplary system to process the GI data collected from sensor assembly along with additional data collected from other sources. An accelerometer and/or gyroscope (604) can provide motion data, an event capturing system (610) can provide event timing data, and other monitoring systems (612) can provide additional physiological data to the data processing unit (520) at various stages such as the heartbeat, the body temperature, or other physical parameters of the patient.

FIG. 6 is a flow chart of an exemplary system to process the GI data collected from the sensor assembly along with additional data collected from other sources. An accelerometer and/or gyroscope (604) can provide motion data, an event capturing system (610) can provide event timing data, and other monitoring systems (612) can provide additional physiological data to the data processing unit (520) at various stages, such as the heartbeat, the body temperature, or other physical parameters of the patient.

A) Accelerometer and/or Gyroscope Data

An accelerometer and/or a gyroscope can be used for collecting motion and position data, serving as an additional input into the data processing unit. Motion data can be used to improve the identification and removal of artifacts, since artifacts are more likely to occur when the subject is moving. Moreover, the gyroscope data provides orientation information, which can be used for determining if a subject is laying down or standing.

One example on how to achieve improved artifact rejection with an accelerometer/gyroscope is to use the Bayesian framework for spectral estimation, which can incorporate information about the likelihood of artifact. In this regard, the noise variance, $\sigma_n^2$, can be large when an artifact in around time n is present, and is smaller elsewhere. Implementing the method for robust spectrotemporal estimation described above:

$$\max_{x_1,\ldots,x_N} -\sum_{n=1}^{N} \frac{1}{2\sigma^2} \| y_n - F_n x_n \|_2^2 + f(x_1, x_2, \ldots, x_N)$$

which has the additional, time-varying $\sigma_n^2$ can be implemented with analogous methods. In this regard, the prior utilizes information from neighboring windows of data to produce better spectrotemporal estimates. By also providing the likelihood of artifact by virtue of specifying $\sigma_n^2$, the prior can more strongly weight the information from neighboring windows, thereby rejecting the artifact in that window of data.

B) Event Data

A mobile device and applications can be used for collecting data, serving as an additional input into the data processing unit. In some embodiments, event timing can be collected by direct user input, or can automatically assessed with another system. Event markers such as meals, sleep, bowel movements, and symptoms, greatly increase the probability of detecting and quantifying abnormalities. For example, a gastric electrical irregularity after a meal but not during fasting may indicate a central nervous system issue, while an dysrhythmia during fasting might indicate a problem with the nerve cells of the stomach controlling the gastric slow wave that leads to peristalsis. For this specific case, the power or magnitude of the 3 cpm (0.05 Hz) component of the EGG can be evaluated shortly before and after the marked event. A drop in the EGG power could indicate an abnormality.

C) Other Physiological Data

Additionally, various other subject physiological data can be collected, including ECG, pulse oximetry, EEG, galvanic skin response (GSR), glucose levels, respiration, pulse oximetry, and temperature. In some embodiments, the ECG or pulse oximetry data provides information about heart rate and heart rate variability, which can capture exercise levels as well as parasympathetic/sympathetic activity of the peripheral nervous system. In some embodiments, the EEG data provides information about sleep and sleep stages. In some embodiments, the GSR data provides information about emotional arousal. In some embodiments, the continuous glucose data can be collected, whereby the blood sugar level response for different meals and meal times can be assessed. In some embodiments, a respiration sensor can be useful for separating the respiration frequency from those of the GI organs, which may sometimes overlap. In some embodiments, a temperature sensor can collect data that can be used to identify various biological rhythms (e.g. circadian rhythm).

This multi-modal physiological data can all be time stamped and combined with the GI data. Example 5 below shows how combining EEG, ECG, and body temperature with the GI data can identify correlations during sleep that are disturbed in a poor night of sleep.

D) Historical and Population Data

Figure 7:
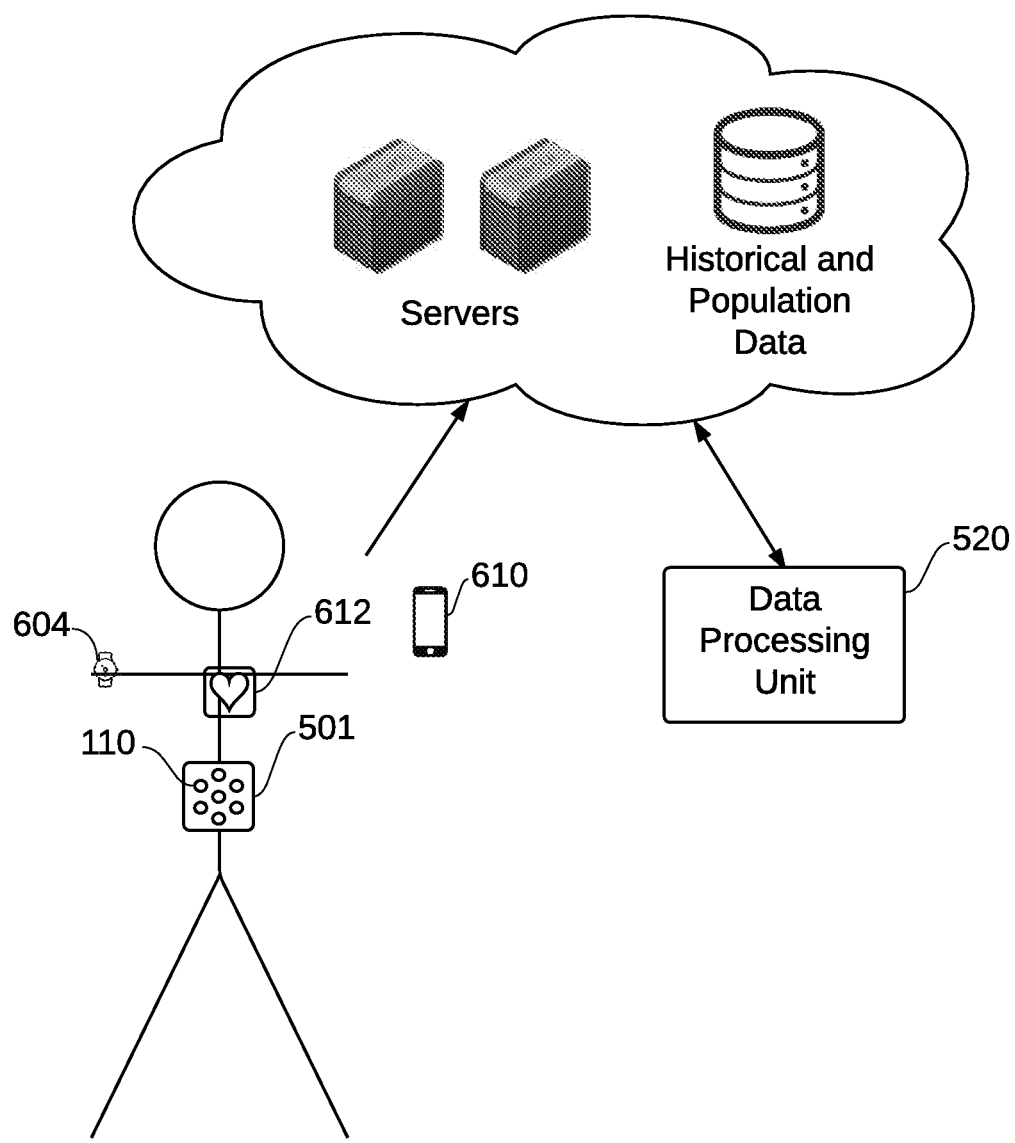
FIG. 7 shows an implementation of the system in FIG. 6 with various wearable devices 604, 501/110 and 612 or a portable device 610 as part of the system. The data processing in this example is performed by one or more servers 520 in the cloud where servers and databases are provided in one or more computer networks (e.g., the web) to facilitate the GI diagnostic processing.

FIG. 7 shows an implementation of the system in FIG. 6 with various wearable devices 604, 501/110 and 612 or a portable device 610 as part of the system. The data processing unit in this example is performed by one or more servers 520 in the cloud, where servers and databases are provided in one or more computer networks (e.g., the web) to facilitate the GI diagnostic processing.

Uploading the data from the system described in FIG. 6 to the cloud enables the creation of a database with data from healthy subjects and patients with GI disorders. The aggregate of this data can be used to evaluate abnormalities. For example, the typical meal or sleep response of the EGG signal can be compared between groups. Moreover, historical data from the same subject can be used as comparison for future recordings to evaluate changes in the GI system over time.

Neural networks are a class of powerful computational approaches within machine learning that are based on a large collection of neural units loosely modeling the way the brain solves problems. Neural networks have very effectively been able to solve complex pattern recognition problems, such as computer vision and speech recognition, at near human level accuracy. A framework similar to the one shown in FIG. 7 would allow the use of neural networks to analyze GI electrophysiological data, since training of these models typically require large labeled datasets and significant computational power.

Applications of Disclosed Technology

Dosing Control

The system and methods described in this disclosure can be used for a closed feedback loop for dosing control of drugs administered either by various administration routes, such as parental administration, topical administration, oral administration, etc. or through a medical device. Currently, the clinician may decide to give a patient medication based on symptoms and the results from clinical testing. Since the currently available functional GI procedures are mostly invasive, costly, and/or require radiation exposure, they are typically not repeated even if they are performed on a subject. The system and methods described in this document are noninvasive, relatively inexpensive, reliable, reproducible, and can quantify GI functions in an ambulatory setting.

Figure 8:
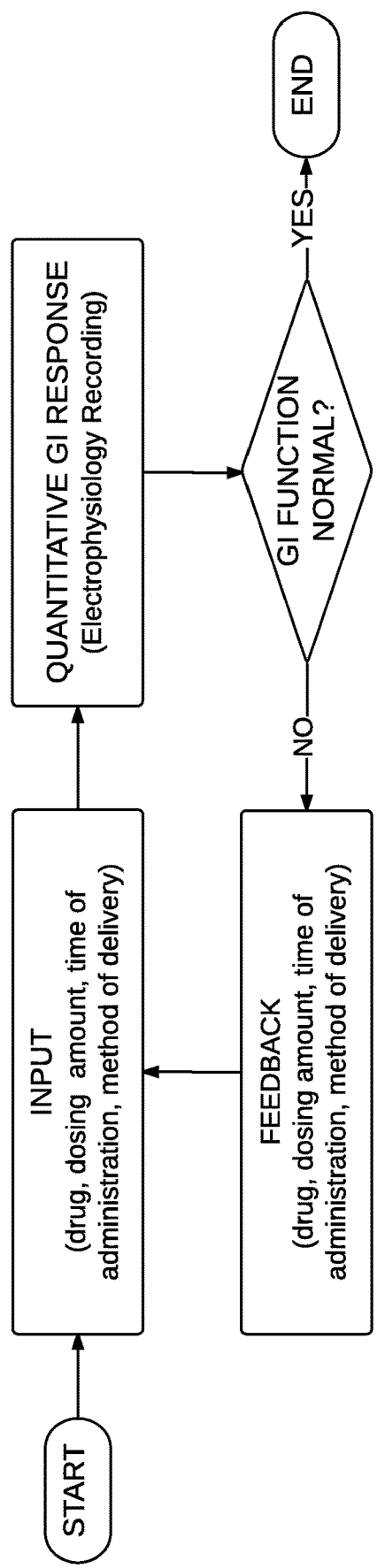
FIG. 8 is a flow chart illustrating that the technology disclosed herein allows the clinician to have a quantitative closed loop system to determine all aspects of medication therapy for the patient.

The technology disclosed herein allows the clinician to have a quantitative closed loop system to determine all aspects of medication therapy for the patient as shown in FIG. 8. For example, the clinician may prescribe certain medication to the patient, quantify its effect on the GI functions over the next 24-48 hours with an electrophysiology recording, and decide to modify the dosage of the medication based on information from both the subjective symptoms described by the patient and the quantitative results from the recording. This process can be iterative with different medications, dosage amounts, time of day for drug administration, and method of delivery (e.g. oral administration, parental injection, etc.) to provide more effective therapy and symptom resolution in a more efficient timeframe. In some embodiments, when used in combination with a medical delivery device, the electrophysiology recording can be processed and fed back to the delivery device as an instruction to automatically or semi-automatically adjust the delivery dosage and/or schedule. One of several extracted quantitative GI features can be used to objectively assess GI function. For example, the restoration of power in the 2-4 cpm frequency band for a stomach recording would indicate the medication had the desired effect.

Thus, the method disclosed herein relates to dosing control and is summarized by the flow chart in FIG. 8. This method entails the steps of administrating a medication to a subject, obtaining the physiological data of GI functions of the subject using the system disclosed herewith for a desired period of time, processing the physiological data thereby to determine the subject's response to the medication, and adjusting the dosing of the medication to the subject. In some embodiments, adjusting the dosing of the medication includes increasing the dosing, decreasing the dosing, discontinuing the dosing, switching to a different medication, adjusting the administration schedule, and/or switching the method of delivery (e.g. from oral administration to injection).

The technology disclosed herein is particularly useful for dosing control in treating chronic conditions such as diabetes, Parkinson's disease, and connective tissue diseases (e.g., scleroderma). Continuous glucose monitors (CGMs) are typically used by diabetic patients to help regulate their blood sugar levels. The technology disclosed herein can be used in conjunction with the continuous glucose monitor as a decision support tool for meal content and timing for medication to avoid conditions resulting in hyperglycemia and hypoglycemia. Likewise, many patients with Parkinson's disease also have motility disorders which affect drug absorption. A lot of Parkinson's patients are old/frail and cannot undergo invasive GI motility testing. The disclosed technology can be used to determine drug dosing for Parkinson's patients. Likewise, scleroderma affects the GI system and can cause diminished GI peristalsis. Therefore, GI functions of scleroderma patients should be monitored and the medication and/or diet should be adjusted accordingly.

Figure 9:
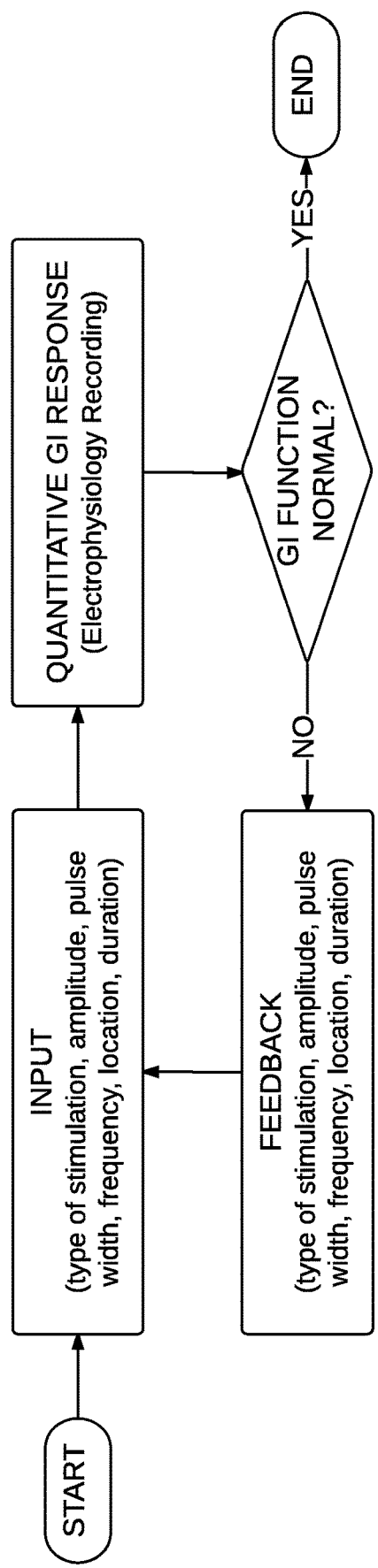
FIG. 9 is a flow chart illustrating that the system and methods described in this disclosure can be used for a closed feedback loop for various stimulation therapies.

The system and methods described in this disclosure can be used for a closed feedback loop for various GI stimulation therapies. FIG. 9 is a flow chart that illustrates this technique. A stimulator can have leads placed directly on the GI organ (similar to the artificial cardiac pacemaker). A stimulator can also stimulate peripheral nerves (e.g. vagus, sacral, and/or tibial nerves). This can be accomplished with invasive or noninvasive devices and different modalities (e.g.

electrical, magnetic, ultrasound, etc.). The GI electrophysiology can be recorded during and after the therapy. The tuning of the parameters of the stimulation (e.g. type of stimulation, amplitude, pulse width, frequency, location, duration) can be iteratively adjusted by the clinician until GI functional issues are resolved using quantitative feedback from the GI electrophysiology recording. For example, stimulation amplitude can be automatically increased up to a predefined limit until power in the 2-4 cpm frequency band for a stomach is restored.

In some embodiments, provided is a method of controlling stimulation therapies, which summarized by the flow chart in FIG. 9. The method entails the steps of administrating the stimulation to a subject, obtaining the physiological data of GI functions of the subject using the system disclosed herewith for a desired period of time, processing the physiological data thereby to determine the subject's response to the stimulation, and adjusting the parameters of the stimulation to the subject. In some embodiments, adjusting of the stimulation parameters include the amplitude, pulse width, duration, frequency, location, and time of day, etc. This may also include stopping of stimulation and/or switching to a different types of stimulation.

Evaluation of Side Effects Caused by Medications

This wearable system can also be used within the context of clinical trials in ambulatory settings to identify candidate therapeutics which not only target a desired clinical outcome, but also have minimal side effects. It is common that therapeutics (e.g. pharmaceutical drugs), whose primary purpose is to target a mechanism or organ outside the GI system, have adverse side effects on the GI system. Currently, the process to identify therapeutics that best balance targeting the mechanism and minimizing GI side effects is subjective, particularly as it relates to GI side effects (where it is common to use patient reported outcomes). This wearable system can be used in ambulatory settings, in conjunction with a clinical trial, to provide objective assessment of GI function. This quantitative information, combined with patient reported outcomes, and the outcomes from the clinical trial regarding the targeting of the desired mechanism, can all be combined to develop more efficient and objective means to select optimal therapeutic agents. Exemplary therapeutic applications include but are not limited to cardiac medications, sleep medications, and chemotherapies for cancer (the latter of which are known to cause nausea and other GI complications). Similarly, this system can be used in conjunction with clinical trials where the targeted system or mechanism has a GI underpinning. In this regard, patient reported outcomes and other conventional ways of assessing drug efficacy can be combined with the said wearable system to provide more detailed statistical and quantitative information about the efficacy of the therapeutic agent.

Many medications result in side effects of the GI system, with associated symptoms such as nausea, constipation, diarrhea, bloating, etc. Examples of such medications include Byetta for diabetes, morphine for pain, all opioids such as Oxycodone, and all dopaminergic drugs for Parkinson's such as Sinemet.

Provided is a method of evaluating side effects of a medication on GI functions. The method entails the steps of administrating a medication to a subject, obtaining the physiological data of GI functions of the subject using the system disclosed herewith for a desired period of time, and processing the physiological data thereby to determine the subject's response to the medication. Diminished power or amplitude in a certain frequency range associated with a GI organ could indicate an adverse side-effect of a medication on GI function.

Guiding GI Recovery after Surgery or Pregnancy

Postoperative ileus is a malfunction of intestinal motility after major intra- or extra-abdominal surgery. Postoperative ileus affects many patients undergoing bowel resection surgery and can cause significant discomfort and prolong the hospital stay. Currently, doctors often wait for the patient to pass gas to determine if his/her digestive system has recovered from the surgery. The technology disclosed herewith provides more accurate timing on when meals can be resumed by the patient post-operation. This can lead to improved patient outcomes, reduced healthcare costs, and faster discharge from the ICU/hospital.

Similarly, pregnant mothers often develop GI motility issues during pregnancy and postpartum, due to gross dislocation of GI organs along with drastic changes in hormone levels. Pregnancy-related changes in motility are present throughout the gastrointestinal tract and are related to increased levels of female sex hormones. For example, one mechanism of the effects of pregnancy on motility is progesterone-induced inhibition of the mobilization of intracellular calcium within smooth muscle cells. The technology disclosed herewith can provide a quantitative assessment of GI function postpartum, with recommendations (e.g. meal timing, meal content, medication, hormones, etc.) to accelerate recovery of the GI system.

A cloud-based approach can be used to assess restoration of GI function. The dynamics of other patients in combination with the previous physiologic activity from the patient can be used to determine when the increase in power in a specific frequency band associated with a GI organ is deemed significantly suggestive that the patient's ileus has changed. In addition, the Bayesian approach described herein is amenable to state-space analysis (e.g. with the Kalman filter), such that real-time estimation can be done to provide timely feedback to the clinician and patient.

Disclosed herewith is a method of treating such conditions. The method includes the steps of obtaining the physiological data of GI functions of the subject using the system disclosed herewith for a desired period of time following an operation procedure or postpartum, processing the physiological data thereby to determine the status of the subject's digestive system, and providing feedback when the functions of the digestive system is restored. In some embodiments, treatment is administered to restore the functions of the digestive system based on automatic or semi-automated feedback.

Guiding Treatment of GI Disorders

Many GI disorders also have overlapping symptoms, making it difficult for clinicians to diagnose and treat the disease. For example, both constipation and gastroparesis can result in nausea. The quantitative physiological monitoring method disclosed herein can differentiate between these diseases and guide the clinical diagnosis and subsequent therapies.

Common GI disorders including, but not limited to, functional dyspepsia, gastroparesis, slow-transit constipation, irritable bowel syndrome, irritable bowel disease, gastritis, and eating disorders can be quantified and diagnosed using the system and methods described in this document. Moreover, since symptoms (e.g. nausea, vomiting, pain, etc.) resulting from various GI disorders are usually transient, the ability to record in an ambulatory setting outside of the clinic setting with relevant event markers (e.g. meals, sleep, bowel movements) greatly increases the probability of detecting and quantifying abnormalities.

Many GI disorders are treatable with a surgical/procedural intervention. For example, pyloric pseudo-obstruction is a condition that is treatable with several endoscopic procedures (e.g. pyloric balloon dilation or Botox injection) spanning several weeks or months. A quantitative assessment of GI function, such as the system and method disclosed, can be used to objectively recommend the cessation of treatment when GI function is restored. A clear indication of pyloric pseudo-obstruction obtained by the physiological monitoring system disclosed herein is shown in Example 4 below.

Thus, the method disclosed herewith relates to guiding the treatment of GI disorders. The method entails the repeated steps of providing a therapy to a subject, obtaining the physiological data of GI functions of the subject using the system disclosed herewith for a desired period of time, and processing the physiological data thereby to determine the subject's response to the therapy.

The following examples illustrate various embodiments of the technology disclosed in this document. By no means the following examples limit the scope of the invention in any way.

Example 1 Robust Spectral Estimation to Improve Single-Channel EGG Reliability

The following experiment demonstrates the advantage of the robust spectral estimation technique and the resulting improvement in EGG reliability.

Figure 10:
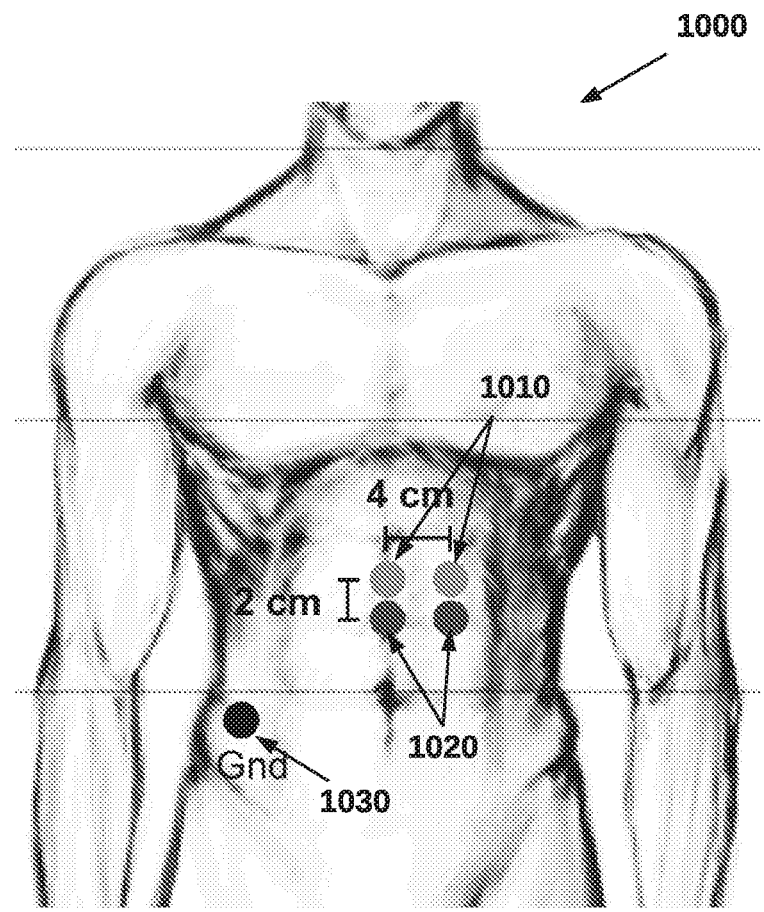
FIG. 10 shows an example of a specific electrode configuration for EGG recording used for one conducted experiment. Two configurations of a bipolar recording electrodes, including measurement and reference electrodes in a pair, are shown: configuration A (1010) and configuration B (1020). The common ground (1030) for both configurations is also shown. These two electrode configurations 1010 and 1020 were recorded simultaneously on a healthy subject to test the sensitivity of an electrode placement according to the disclosed technology. Configuration 1020 is placed about 2 cm below configuration 1010.

FIG. 10 shows an example of a specific electrode configuration for EGG recording used for one conducted experiment. In FIG. 10, two configurations of a bipolar recording electrodes, including measurement and reference electrodes in a pair, are shown: configuration A (1010) and configuration B (1020). The common ground (1030) for both configurations is also shown. These two electrode configurations 1010 and 1020 were recorded simultaneously on a healthy subject to test the sensitivity of an electrode placement according to the disclosed technology. Configuration 1020 is placed about 2 cm below configuration 1010. The subject's skin was prepped with NuPrep® to reduce skin impedance and improve signal quality. After an overnight fast, the EGG was recorded 30/60 minutes pre/post-prandial. A test meal including an energy bar and 8 ounces of water was provided to the subject. The subject was in a reclined position throughout the recording and the subject's motion was kept to a minimum.

Figure 11:
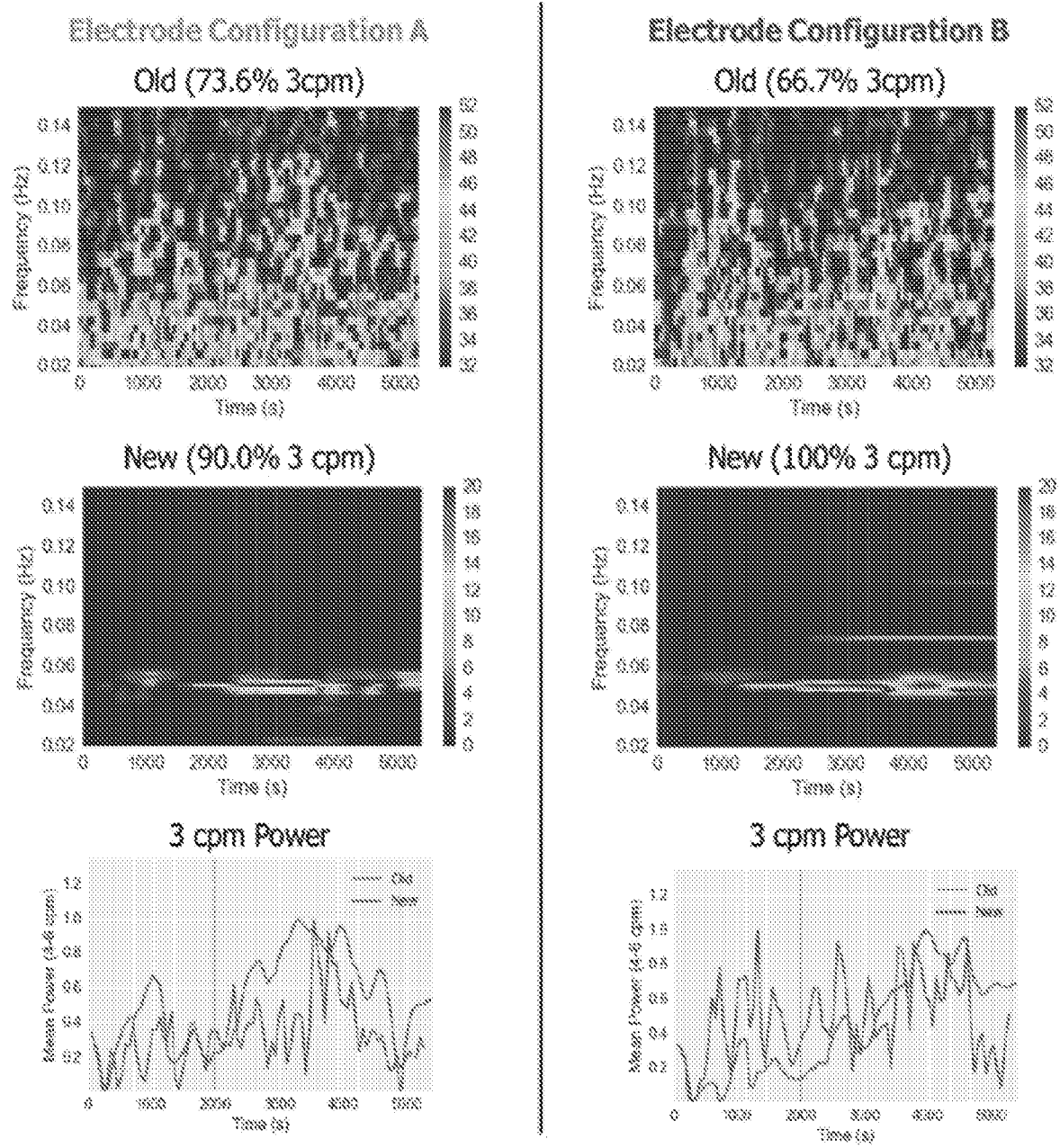
FIG. 11 demonstrates that the robust spectral estimation technique disclosed herein resulted in improvement in EGG reliability. The results of the EGG recordings from the electrode configuration in FIG. 10 are shown. A comparison of the traditional protocol of analyzing the EGG recording using short-time Fourier transform (STFT) (top panel) and the robust spectral estimation of the EGG recording as disclosed herein (middle panel) is shown. The power in the 3 cpm frequency band across time, reflecting the intensity of stomach activity (bottom panel) is also shown. The left and right columns are electrode configurations A and B, respectively.

FIG. 11 shows the results of the EGG recordings from the electrode configuration in FIG. 10. A comparison of the traditional protocol of analyzing the EGG recording using short-time Fourier transform (STFT) (top panel) and the robust spectral estimation of the EGG recording as disclosed herein (middle panel) is shown. The power in the 3 cpm frequency band across time, reflecting the intensity of stomach activity (bottom panel) is also shown. The left and right columns are electrode configurations A and B, respectively.

A short-time Fourier transform (STFT) with overlapping windows was used to estimate the frequency components of an EGG signal. Although analysis with sliding windows was universally accepted, this approach had several drawbacks when applied to analyze the EGG data. First, the spectral estimates computed in a given window did not use the estimates computed in adjacent windows, hence the resulting spectral representations did not fully capture the degree of smoothness inherent in the underlying signal. Second, the uncertainty principle imposed stringent limits on the spectral resolution achievable by Fourier-based methods within a window. Because the spectral resolution was inversely proportional to the window length, sliding window based spectral analyses were problematic when the signal dynamics occurred at a shorter time-scale than the window length. Third, based on the physiology underlying the EGG signal, the objective was to compute a time-frequency representation that was piecewise smooth or continuous in time and sparse in frequency. The spectral estimation procedures disclosed herein were not specifically tailored to achieve smoothness in time and sparsity in frequency. Subsequently, by formulating a Bayesian estimation problem with a prior distribution that yielded maximum a posteriori (MAP) spectral estimates that were continuous in time yet sparse in frequency, more robust estimates of EGG frequency and amplitude were achieved.

The percentage of time the dominant frequency is between 2 and 4 cpm was around 70% as reported by the conventional STFT spectrogram (top panel). Slightly shifting the electrodes by 2 cm dropped the percentage below the 70% threshold that was typically used to assess whether EGG is normal. Also, no clear power increase was observed after the meal for the STFT spectrogram (bottom panel). The robust spectral estimation (middle panel) not only correctly identified the dominant 3 cpm frequency throughout the recording, but also displayed a distinct postprandial power increase. Moreover, the robust spectrogram was not as sensitive to electrode placement as the conventional EGG. In this subject, the STFT spectrogram resulted in a false positive while the robust spectrogram unmistakably revealed normal EGG activity.

Example 2 Artifact Rejection and Robust Spectral Estimation Improves Multiple Channel EGG Reliability The antroduodenal manometry (ADM) procedure measures GI contractions by measuring pressure at several points inside the stomach and small intestines. The smooth muscle contractions in the stomach and the intestines are initiated by the electrical activity (i.e. a contraction cannot exist without coordinated electrical activity). Therefore, in a healthy stomach, the EGG power or amplitude (represented by the magnitude of electrical activity near 3 cpm frequency) and intragastric pressure amplitude representing muscle contraction strength should be correlated.

The following experiment was performed on a healthy subject to quantify the improvement in the EGG when using the approach disclosed herewith with multiple channels. Multi-channel EGG was recorded with a 5 by 5 array of skin-mounted electrodes positioned over the stomach during an ADM study. ADM was performed with a flexible catheter comprising of 8 water-perfused channels. A blind-source separation (BSS) algorithm and robust spectral analysis was applied to isolate the gastric electrical activity. Linear regression between the extracted gastric signal and intragastric pressure measured with the catheter was used to quantify performance of the methodology.

BSS was successfully applied to multichannel EGG to improve its signal-to-noise ratio (SNR) and to remove confounding artifacts. A regression analysis of the standard single-channel approach with no artifact removal showed a poor correlation between EGG and ADM, which was significantly improved after applying BSS and the robust spectrogram ($r=0.37$, $p=2.3\times10^{-15}$).

Figure 12A:
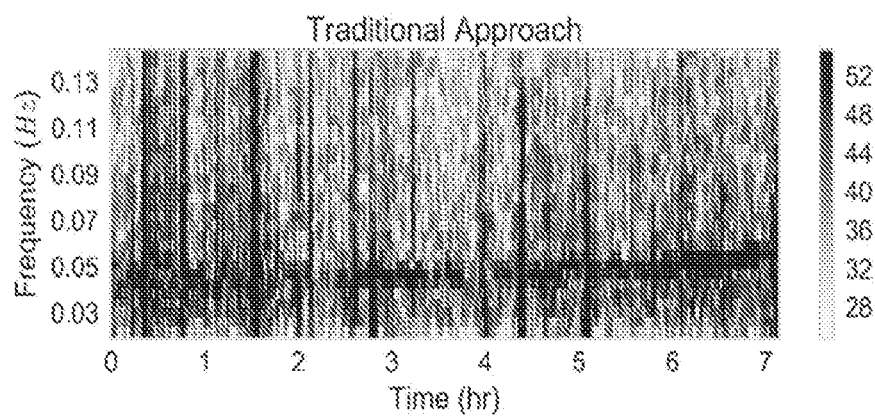
FIG. 12 illustrates experimental data obtained using a multiple channel EGG monitoring technique disclosed herein. The improvement in SNR is shown in FIG. 12A and FIG. 12B and the relationship between the two modalities (black: EGG 3 cpm amplitude; grey: invasive pressure) is shown in FIG. 12C. The vertical lines in FIG. 12A represent the artifacts from movement that were removed in FIG. 12B with approach disclosed in this document.
Figure 12B:
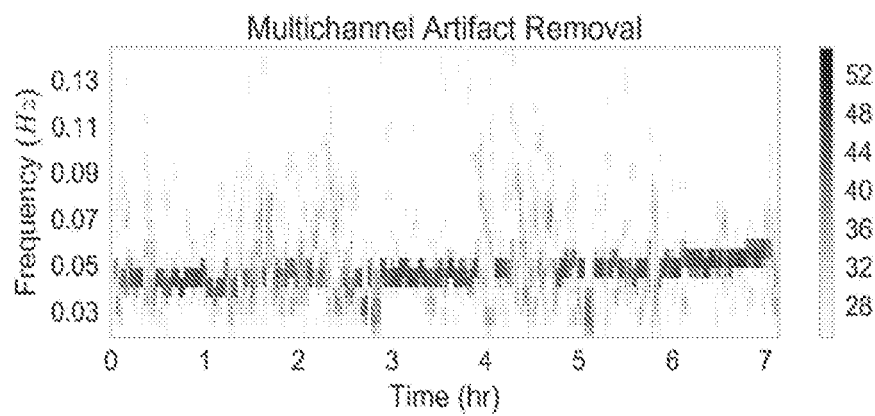
Figure 12C:
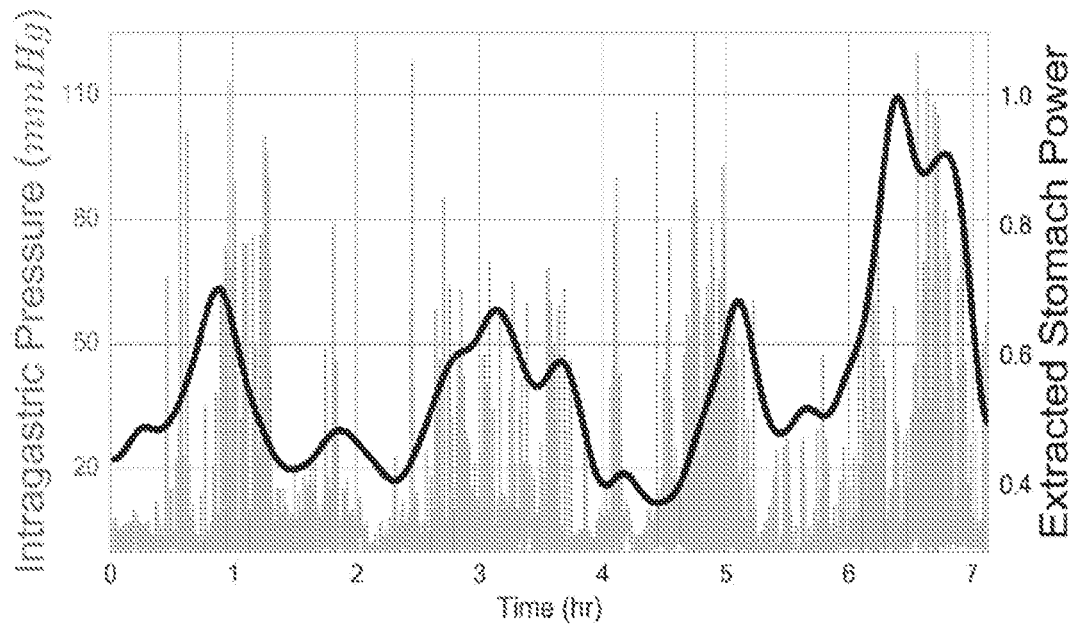

FIG. 12 illustrates experimental data for this experiment. The improvement in SNR can be clearly seen in FIGS. 12A and 12B and the relationship between the two modalities (black: extracted EGG power near 3 cpm; grey: invasive pressure recorded by ADM) is shown in FIG. 12C. The dark vertical lines in FIG. 12A represent the artifacts from movement. Both artifacts and noise were removed in FIG. 12B using the approaches disclosed in this document. No study has reported this correlation using the traditional EGG approaches.

Figure 13:
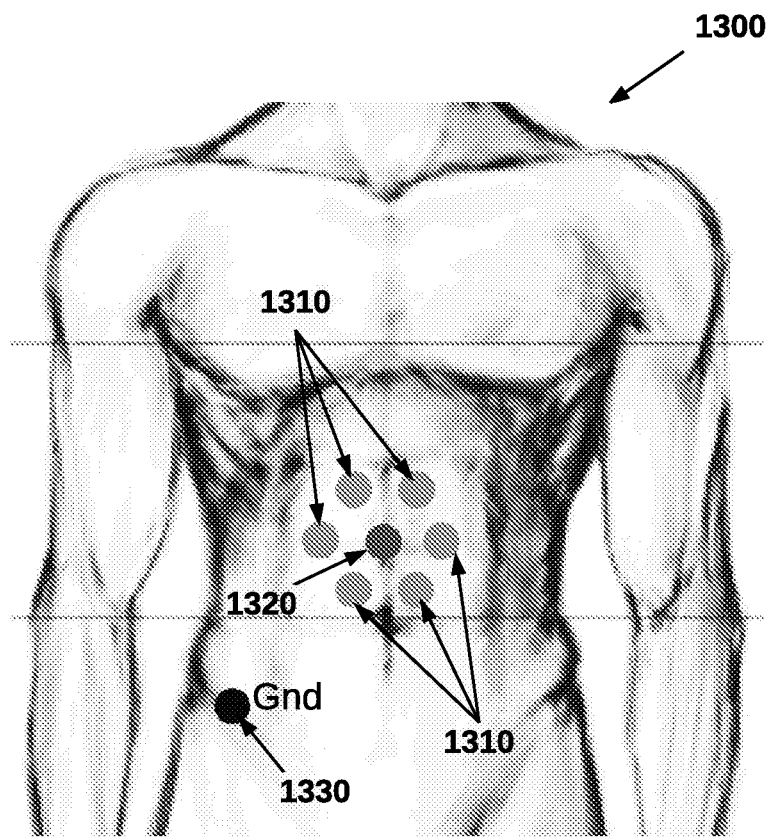
FIG. 13 demonstrates an exemplary wearable system having a circular electrode array arrangement. Six pre-gelled measurement electrodes 1310 were placed in a radial circular array on the subject, with a common reference electrode 1320 in the middle and a common ground electrode 1330 on the right hip bone. The center electrode was located 10 cm below the xiphoid and the spacing between measurement electrodes was 4 cm.

Example 3 Artifact Rejection and Robust Spectral Estimation Enables Ambulatory Monitoring This methodology described herein enables the robust recording the GI functional activity in an ambulatory, in an unrestricted setting. FIG. 2B and FIG. 13 demonstrate an exemplary wearable system having a circular electrode array arrangement and an easy-to-use application for a patient to document events or activities such as meal, snack, bowel movement, sleep, etc. within a certain period of time (e.g. within 24-hour recording time), such that the patient can be monitored in an ambulatory fashion. The preliminary results demonstrate the feasibility of the wearable system at robustly detecting gastric activity, as well as using a smart-phone App that was developed to document event times that influenced gastrointestinal function.

In the example in FIG. 13, six pre-gelled measurement electrodes 1310 were placed in a radial circular array on the subject, with a common reference electrode 1320 in the middle and a common ground electrode 1330 on the right hip bone. The center electrode was located 10 cm below the xiphoid and the spacing between measurement electrodes was 4 cm. The EGG was recorded for a 24-hour period with a custom, battery-powered wearable system.

Figure 14:
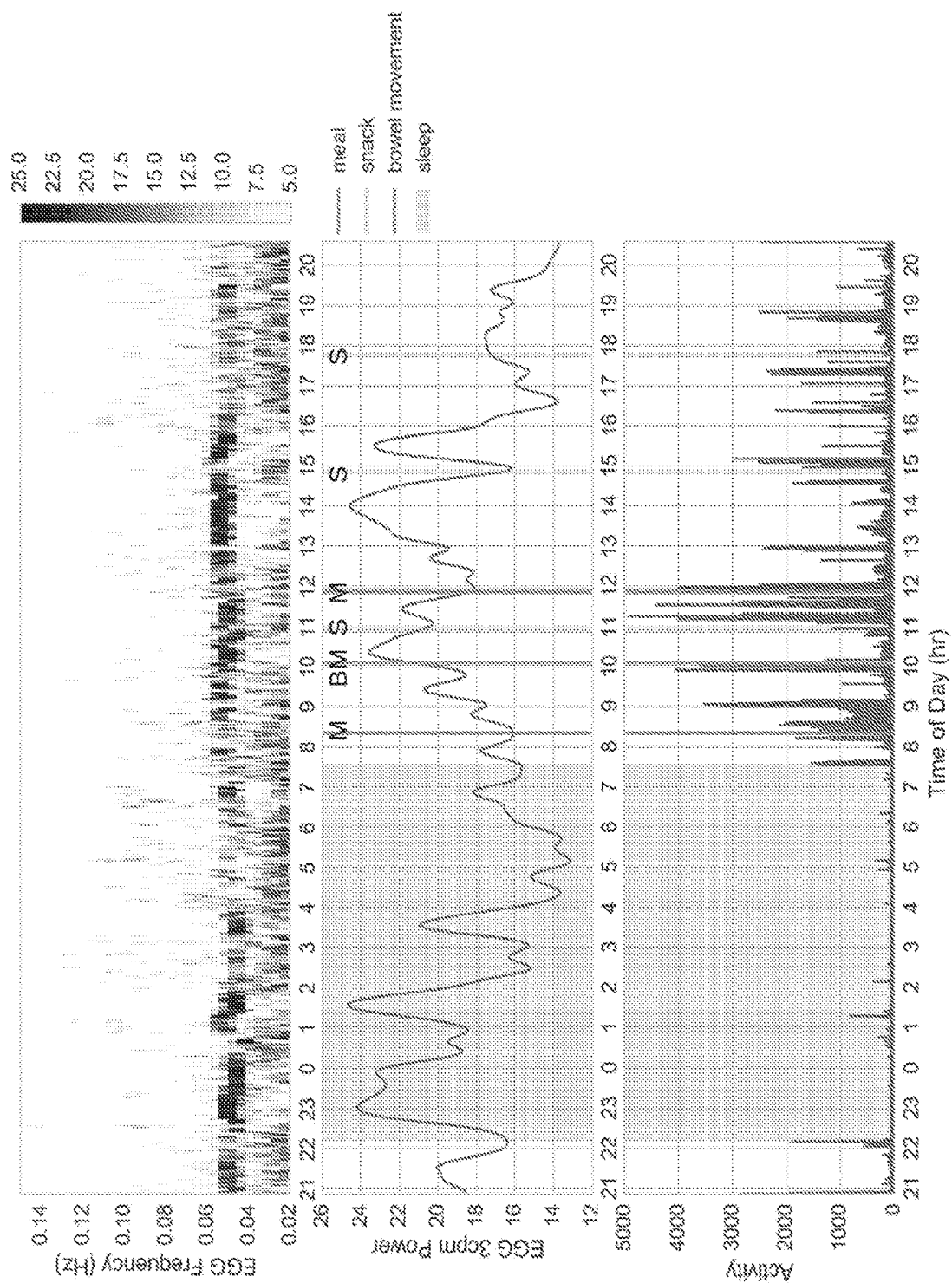
FIG. 14 shows an example of an EGG recording by the wearable system for a healthy subject for 24 hours. The top panel shows the robust multichannel spectrogram. The middle panel shows the extracted stomach activity with event markers such as sleep (shaded area), meal (the line(s) labeled "M"), snack (the line(s) labeled "S"), and bowel movement (the line(s) labeled "BM"). The bottom panel shows the accelerometer data which demonstrates very little activity during sleep.

An example of such an EGG recording by the wearable system for a healthy subject for 24 hours is shown in FIG. 14. The top panel shows the robust multichannel spectrogram as described above. The middle panel shows the extracted stomach activity with event markers such as sleep, meal, snack, and bowel movement. The bottom panel shows the accelerometer data which demonstrates very little activity during sleep.

Figure 15:
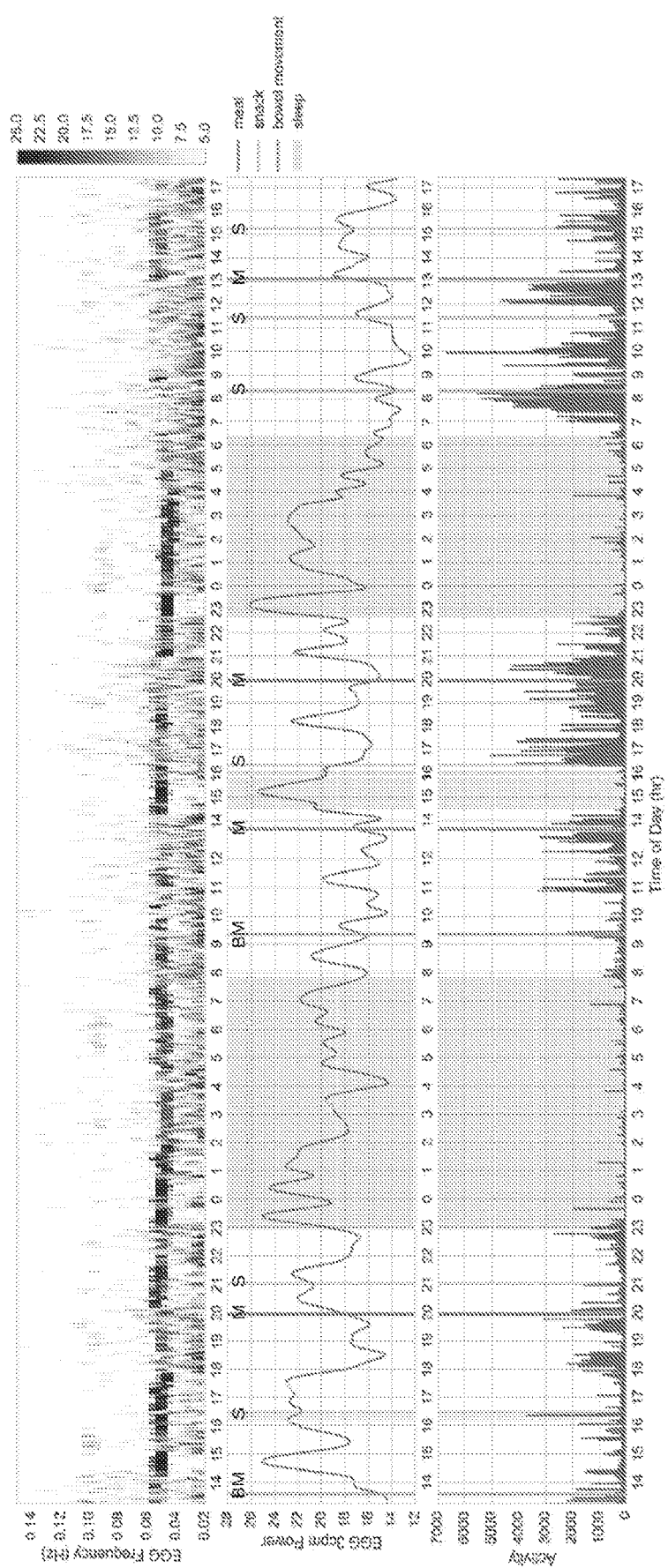
FIG. 15 shows an example of an EGG recording by the wearable system for a healthy subject for a period of over 50 hours. The top panel shows the robust multichannel spectrogram, the middle panel is the extract stomach activity and event markers such as sleep (shaded area), meal (the line(s) labeled "M"), snack (the line(s) labeled "S"), and bowel movement (the line(s) labeled "BM"), and the bottom panel reflects the activity level from the accelerometer.

The same procedure as described above was also applied to a different healthy subject for a period of over 50 hours. The results are shown in FIG. 15. Similarly, the top panel shows the robust multichannel spectrogram, the middle panel is the extracted stomach activity with event markers, and the bottom panel reflects the activity level from the accelerometer. This demonstrates feasibility of reliable long-term recordings.

Example 4 Ambulatory Monitoring System Results in a Clear Indication of Disease State Pyloric spasm/intermittent obstruction is a treatable condition, for example, treatable with pyloric balloon dilation or Botox injection, yet this condition is very difficult to diagnose. Our ambulatory monitoring system was used to record the stomach activity of a patient with diagnosed pyloric pseudo-obstruction and two healthy controls. The electrode configuration shown in FIG. 13 was used. Six pre-gelled measurement electrodes 1310 were placed in a radial circular array on the subject, with a common reference electrode 1320 in the middle and a common ground electrode 1330 on the right hip bone. The center electrode was located 10 cm below the xiphoid and the spacing between measurement electrodes was 4 cm. The EGG was recorded for a 24-hour period with a custom, battery-powered wearable system.

Figure 16A:
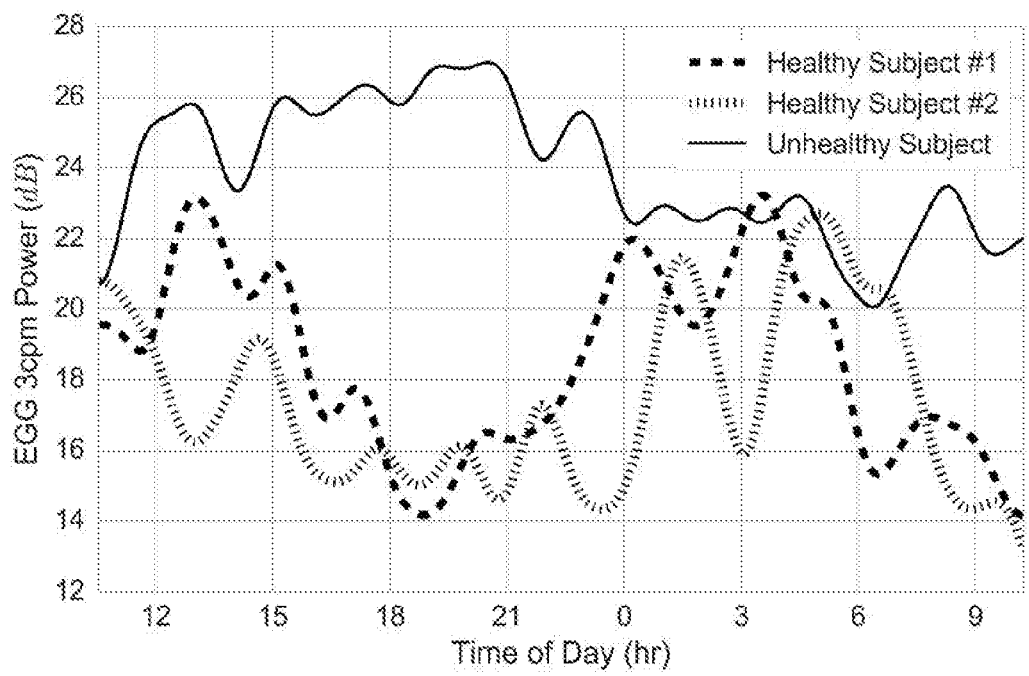
FIG. 16A represents the extracted EGG 3 cpm power throughout the day, starting shortly after 11 am. The solid line represents an unhealthy subject, whereas the dotted and dashed lines represent two healthy subjects.
Figure 16B:
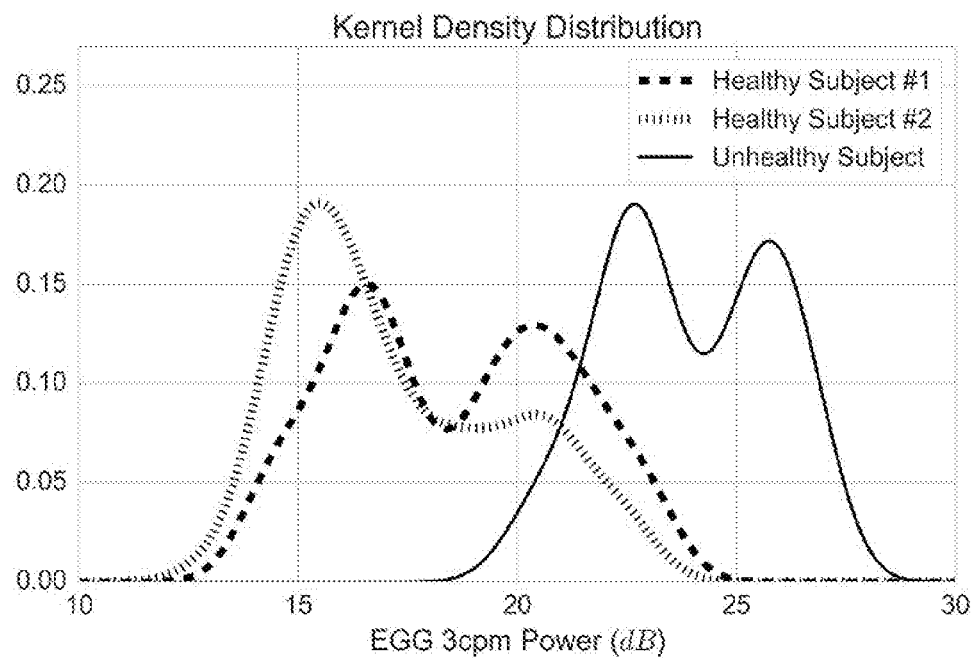
FIG. 16B is the corresponding distribution of 3 cpm EGG power. The solid line represents the unhealthy subject, whereas the dotted and dashed lines represent two healthy subjects.

The patient with pyloric spasm/intermittent obstruction had an abnormally high amplitude gastric slow wave occurring continuously throughout the recording period, a physiologically anticipated result. With the recording and data analysis method disclosed herein, a 24-hour signature pattern of pyloric spasm/intermittent obstruction was detected for the first time. FIG. 16A shows the extracted EGG power near the 3 cpm frequency for the three subjects over a 24-hour period, with the recordings starting shortly after 11 am. FIG. 16B is a histogram representation of the same data, demonstrating that the patient with pyloric pseudo-obstruction exhibited significantly higher EGG power near 3 cpm throughout the recording compared to the healthy controls. This example shows a real clinical utility that was enabled with the methodology disclosed in this document.

Example 5 Ambulatory Monitoring Combined with Additional Inputs (ECG, EEG, Temperature)

The GI monitoring system can be used in conjunction with other monitoring systems. The EEG, EGG, ECG, and body temperature was recorded on a healthy subject on two consecutive nights of sleep. The EEG was recorded with two pre-gelled electrodes (measurement and reference) placed on the forehead 5 cm apart. The EGG was recorded using the configuration shown in FIG. 13. Six pre-gelled measurement electrodes 1310 were placed in a radial circular array on the subject, with a common reference electrode 1320 in the middle and a common ground electrode 1330 on the right hip bone. Both the EEG and EGG shared a common ground and were recorded with the same device. The heart rate was extracted from the R-peaks that were detected by the EGG recording. Body temperature was measured axially using a probe with 0.0625° C. resolution, logging once every minute. The recordings and extracted features were time-synchronized and plotted.

Figure 17:
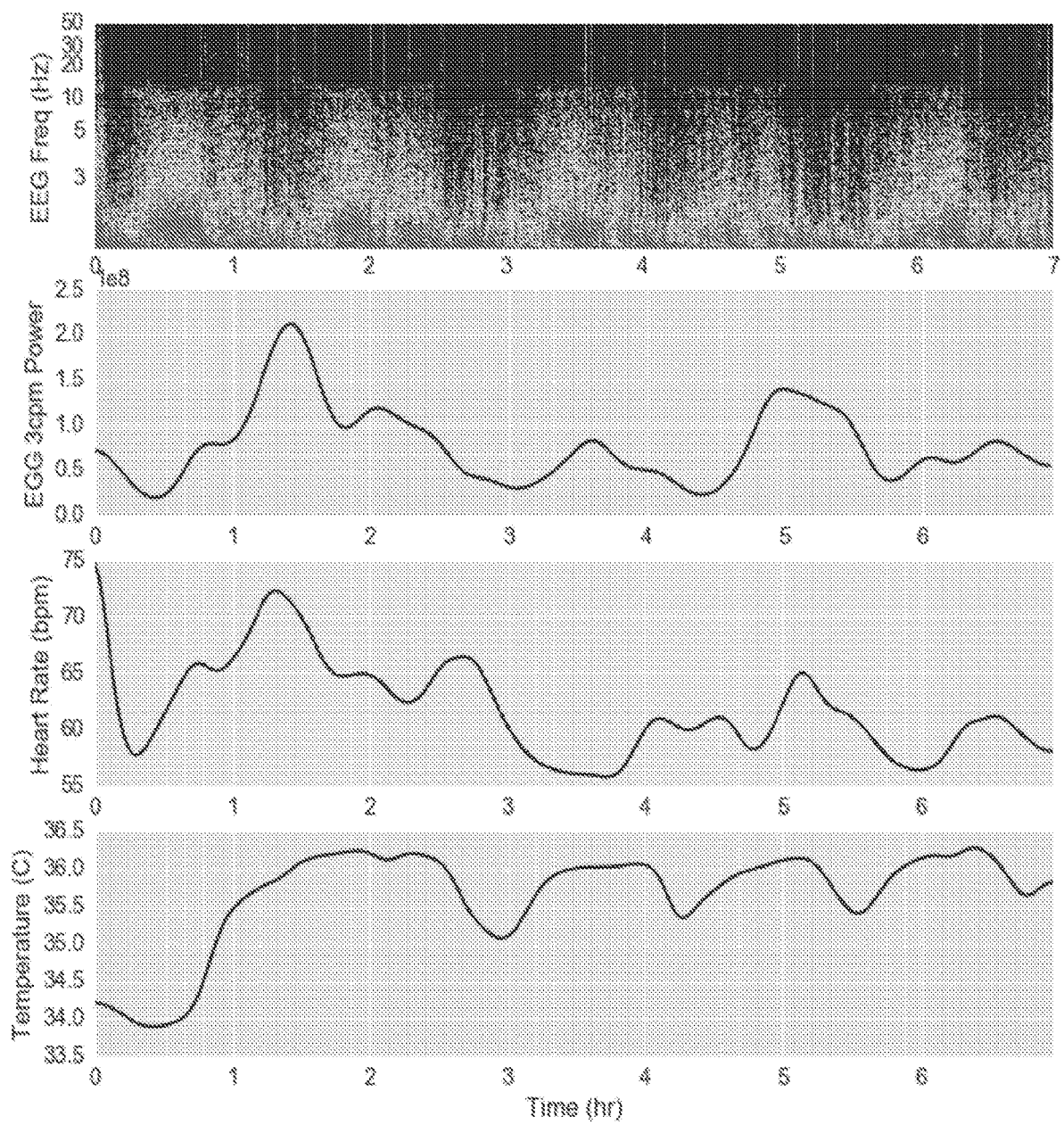
FIG. 17 represents a good night of sleep, as reported by the subject. The subject slept through the night and woke up naturally in the morning. The first panel is a spectrotemporal representation of the EEG data. The second panel is the extracted EGG power. The third panel is the extracted heart rate in bpm. Finally, the fourth panel is the axial temperature in ° C.
Figure 18:
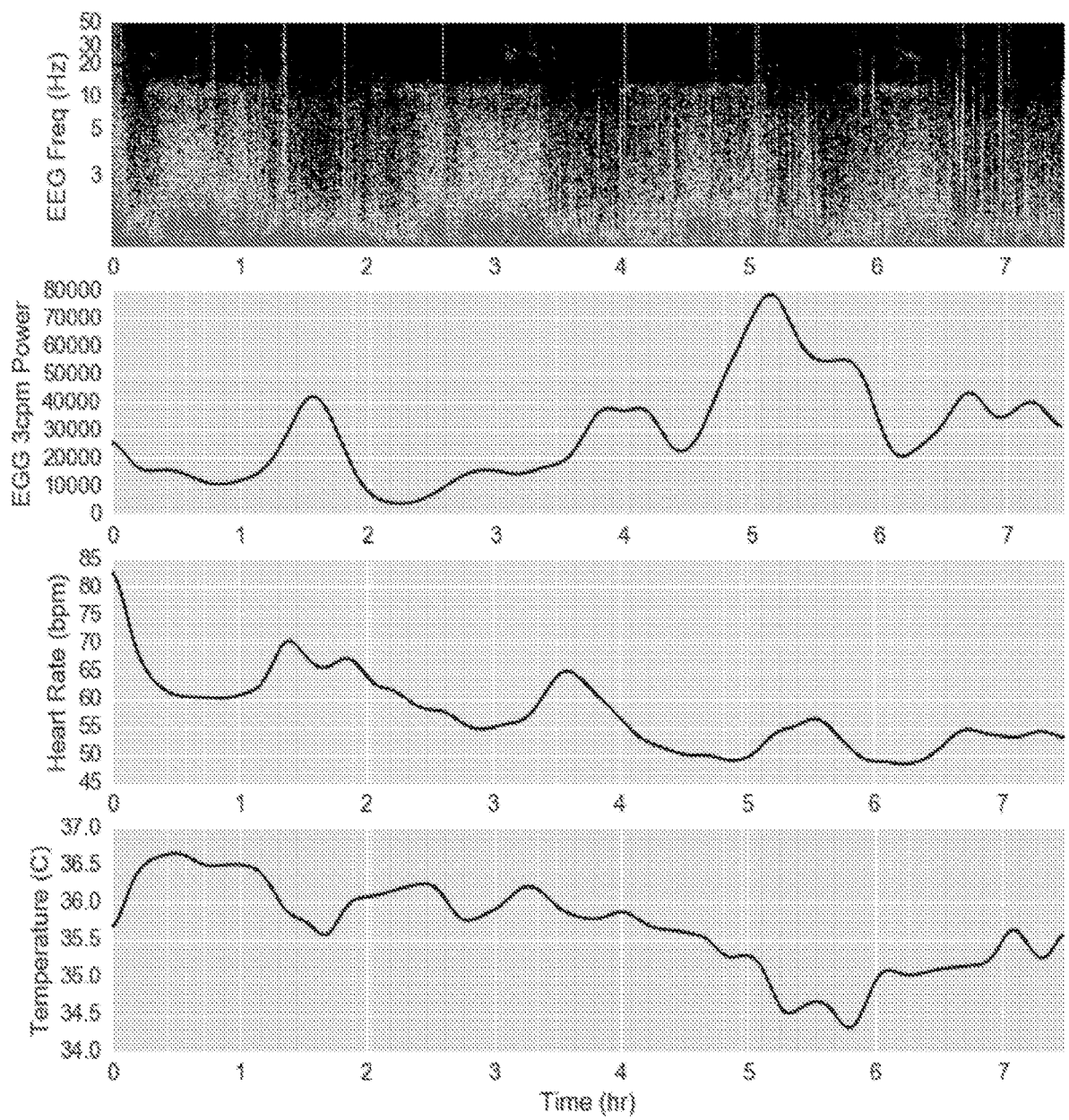
FIG. 18 represents a poor night of sleep, as reported by the subject. The subject woke up multiple times and reported being hot and uncomfortable. The first panel is a spectrotemporal representation of the EEG data. The second panel is the extracted EGG power. The third panel is the extracted heart rate in bpm. Finally, the fourth panel is the axial temperature in ° C.

FIG. 17 represents a good night of sleep, as reported by the subject. The subject slept through the night and woke up naturally in the morning. The first panel is a spectrotemporal representation of the EEG data. The EEG data can be used to extract sleep staging across time (e.g. hypnogram). The second panel is the extracted EGG power. The third panel is the extracted heart rate in bpm. Finally, the fourth panel is the axial temperature in ° C. Five complete sleep cycles can be observed, with structured changes in EGG, heart rate, and body temperature. FIG. 18 represents a poor night of sleep, as reported by the subject. The subject woke up multiple times and reported being hot and uncomfortable. Similar to FIG. 17, the four panels represent the EEG, EGG, heart rate, and body temperature. In this figure, only four cycles of sleep are observed. Unlike the good night of sleep, the stomach power increases as the night progresses while the body temperature decreases, reaching their respective maximum and minimum points at approximately 5 hours.

These types of recordings allow us to assess various aspects of a person's physiology along with their coupling. In this experiment, the poor night of sleep was confirmed by the disrupted relationships between the different modalities. This example demonstrates that multiple physiological measurements can provide improved feature extraction for the assessment of health.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed are techniques and structures as described and shown, including:

1. A method of monitoring a gastrointestinal function of a subject, comprising:
   receiving, at a data processing unit comprising a processor and a memory in communication with the processor, an electrophysiological signal obtained from one or more sensors in contact with skin surface of the subject over at least a portion of the subject's abdominal region;
   analyzing the received electrophysiological signal by identifying and removing undesired artifacts in the received electrophysiological signal to produce a waveform;
   determining one or more spectral features from the waveform;
   producing a data set indicative of a gastrointestinal function of the subject by extracting a quantitative feature from at least some of the one or more spectral features; and
   determining a qualitative output indicative of a quality of sleep related to parasympathetic and sympathetic activity of the peripheral nervous system of the subject from the data set indicative of the subject's gastrointestinal function by analyzing a trend or variability in a change of electrogastrogram (EGG) power over a time period during the subject's sleep.

2. The method of claim 1, wherein the one or more spectral features are estimated using a Bayesian estimation problem.

3. The method of claim 1, wherein the determining the one or more spectral features includes computing a time-varying spectral decomposition of the waveform and selecting one or more smoothed and de-noised spectral estimates.

4. The method of claim 1, wherein the one or more spectral features include Fourier coefficients across time.

5. The method of claim 1, wherein extracting the quantitative feature includes selecting the quantitative feature from a respective spectral feature, and determining a polynomial function of the selected quantitative feature.

6. The method of claim 5, wherein the selected quantitative feature includes a particular frequency band of the respective spectral feature, and the polynomial function of the selected quantitative feature includes the square of the magnitude of the energy in the particular frequency band.

7. The method of claim 1, further comprising:
   receiving, at the data processing unit, from a motion sensor attached to the subject, motion data indicative of a position, orientation or movement of the subject; and
   correlating the motion data with the received electrophysiological signal to identify and remove the undesired artifacts to produce the waveform.

8. The method of claim 1 further comprising:
   receiving, at the data processing unit, event data associated with an activity by the subject that occurs during acquisition of the electrophysiological signal; and
   including the event data in association with the determined spectral data in the data set.

9. The method of claim 8, wherein the activity by the subject includes a meal, a physical activity, a symptom, or bowel movement.

10. The method of claim 1, further comprising:
    receiving, at the data processing unit, ancillary physiological data measured from the subject during acquisition of the electrophysiological signal; and
    processing the ancillary physiological data with the determined spectral data to produce the data set.

11. The method of claim 10, wherein the ancillary physiological data includes ECG data, EEG data, EMG data, GSR data, glucose data, pulse oximetry data, respiratory data or temperature data.

12. The method of claim 1, further comprising:
    processing the data set to generate a displayable output illustrative of the gastrointestinal function of the subject.

13. The method of claim 1, further comprising:
    processing the data set of the subject with a population data set of a plurality of subjects with and/or without gastrointestinal dysfunction; and
    producing a second data set of the subject including comparison markers based on comparative analysis of the data set with the population data set.

14. The method of claim 1, further comprising:
    processing the data set of the subject with historical data set of past data of the subject, the historical data set including normal gastrointestinal function data and/or abnormal gastrointestinal dysfunction data; and
    producing a second data set of the subject including comparison markers based on comparative analysis of the data set with the historical data set.

15. The method of claim 1, wherein the identifying and removing the undesired artifacts in the electrophysiological signals include separating a set of source signals associated with gastrointestinal activities of the subject from a set of mixed signals comprising a linear mixture of individual electrophysiological signals obtained by the one or more sensors.

16. The method of claim 1, wherein the one or more sensors in contact with skin surface of the subject over at least a portion of the subject's abdominal region that obtain the electrophysiological signal include a plurality of electrophysiological electrodes of a gastrointestinal sensor assembly, and the gastrointestinal sensor assembly is in communication with the data processing unit.

* * * * *